US006355433B1

(12) United States Patent
Xu et al.

(10) Patent No.: US 6,355,433 B1
(45) Date of Patent: Mar. 12, 2002

(54) DETERMINATION OF NUCLEOTIDE SEQUENCE VARIATIONS THROUGH LIMITED PRIMER EXTENSION

(75) Inventors: Hua Xu, Sunnyvale; Alexander N. Glazer, Orinda, both of CA (US)

(73) Assignee: DNA Sciences, Inc., CA (US)

( * ) Notice: Subject to any disclaimer, the term of this patent is extended or adjusted under 35 U.S.C. 154(b) by 0 days.

(21) Appl. No.: 09/586,125

(22) Filed: Jun. 2, 2000

(51) Int. Cl.[7] ............................................... C12Q 1/68
(52) U.S. Cl. .......................... 435/6; 435/5; 435/91.1; 435/91.2; 436/536; 436/518
(58) Field of Search .................. 435/6, 5, 91.1, 435/91.2; 436/536, 518

(56) References Cited

U.S. PATENT DOCUMENTS

| 4,656,127 A | 4/1987 | Mundy |
| 4,863,849 A | 9/1989 | Melamede |

(List continued on next page.)

FOREIGN PATENT DOCUMENTS

| EP | 0 229 943 | 7/1987 |
| EP | 0 601 889 | 6/1994 |
| EP | 0 412 883 | 11/1996 |
| GB | 2 252 407 | 8/1992 |
| WO | WO 90/09455 | 8/1990 |
| WO | WO 90/13666 | 11/1990 |
| WO | WO 91/13075 | 9/1991 |
| WO | WO 92/15712 | 9/1992 |
| WO | WO 92/16657 | 10/1992 |
| WO | WO 93/05183 | 3/1993 |
| WO | WO 93/25563 | 12/1993 |
| WO | WO 97/22719 | 6/1997 |
| WO | WO 98/59066 | 12/1998 |

OTHER PUBLICATIONS

Ausubel, F.M. (1988) "Polyacrylamide gel Electrophoresis" in Current Protocols in Molecular Biology, John Wiley and Sons pp. 6.36–6.38 *Gel Electrophoresis of DNA*.

Ambrose, B.J.B. and Pless, R. C.; DNA Sequencing: Chemical Methods, *Methods in Enzymology*, (1987) vol. 152, pp. 522–539.

Brand, Eve et al., Structural Analysis and Evaluation Of The Aldosterone Synthase Gene In Hypertension, *Hypyertension*, (1998) vol. 32, pp. 198–204.

Cardullo, R.A. et al., Detection of Nucleic Acid Hybridization by Nonradiative Fluorescence Resonance Energy Transfer, *Proc. Natl. Acad. Sci. USA*, Dec. 1988, vol. 85, pp. 8790–8794.

(List continued on next page.)

*Primary Examiner*—W. Gary Jones
*Assistant Examiner*—Janell E. Taylor

(57) ABSTRACT

The present invention provides methods and kits for determining the identity of a nucleotide at a variant site in a target nucleic acid of interest, including, for example, point mutations and single nucleotide polymorphisms. The methods involve conducting template-dependent extension reactions in the presence of a mixture of nucleotides that include at least one labeled extendible nucleotide and at least one labeled non-extendible nucleotide that are selected to be complementary to the nucleotides that potentially occupy the variant site. The particular labeled nucleotide incorporated into the extension products is characteristic of the nucleotide at the variant site. In addition to their utility in analyzing point mutations and single nucleotide polymorphisms, the methods and kits of the invention have utility in a variety of other applications in which specific nucleotide sequence information is of value, including, for example, paternity disputes, prenatal testing, forensic analysis and detection of pathogens.

45 Claims, 8 Drawing Sheets

U.S. PATENT DOCUMENTS

| | | |
|---|---|---|
| 4,962,037 A | 10/1990 | Jett et al. |
| 5,137,806 A | 8/1992 | LeMaistre et al. |
| 5,171,534 A | 12/1992 | Smith et al. |
| 5,210,015 A | 5/1993 | Gelfand et al. |
| 5,219,727 A | 6/1993 | Wang et al. |
| 5,302,509 A | 4/1994 | Cheeseman |
| 5,487,972 A | 1/1996 | Gelfand et al. |
| 5,518,900 A | 5/1996 | Nikiforov et al. |
| 5,538,848 A | 7/1996 | Livak et al. |
| 5,547,839 A | 8/1996 | Dower et al. |
| 5,639,611 A | 6/1997 | Wallace et al. |
| 5,654,419 A | 8/1997 | Mathies |
| 5,688,648 A | 11/1997 | Mathies |
| 5,707,804 A | 1/1998 | Mathies |
| 5,710,028 A | 1/1998 | Eyal et al. |
| 5,728,528 A | 3/1998 | Mathies et al. |
| 5,747,249 A | 5/1998 | Smith et al. |
| 5,804,375 A | 9/1998 | Gelfand et al. |
| 5,821,058 A | 10/1998 | Smith et al. |
| 5,827,653 A | 10/1998 | Sammes et al. |
| 5,846,710 A | 12/1998 | Bajaj |
| 5,853,992 A | 12/1998 | Glazer et al. |
| 5,856,092 A | 1/1999 | Dale et al. |
| 5,863,736 A | 1/1999 | Haaland |
| 5,866,336 A | 2/1999 | Nazarenko et al. |
| 5,876,930 A | 3/1999 | Livak et al. |
| 5,885,775 A | 3/1999 | Haff et al. |
| 5,888,819 A | 3/1999 | Goelet et al. |
| 5,891,629 A | 4/1999 | Goldrick |
| 5,945,283 A | 8/1999 | Kwok et al. |
| 5,981,186 A | 11/1999 | Gabe et al. |
| 6,004,744 A | 12/1999 | Goelet et al. |
| 6,013,431 A | 1/2000 | Suderlund et al. |
| 6,027,890 A * | 2/2000 | Ness et al. ............... 435/6 |

OTHER PUBLICATIONS

Chen, Xiangning and Kwok; Pui–Yan; Homogeneous Genotyping Assays For Single Nucleotide Polymorphisms With Fluorescence Resonance Energy Transfer Detection, *Genetic Analysis: Biomolecular Engineering,* (1999) vol. 14, pp. 157–163.

Chen, Xiangning and Kwok, Pui–Yan; Template–directed Dye–terminator Incorporation (TDI) Assay: A Homogenous DNA Diagnostic Method Based On Fluorescence Resonanace Energy Transer, *Nucleic Acids Research* (1997) vol. 25, No. 2, pp. 347–353.

Chen, Xiangning et al., A Homogeneous, Ligase–Mediated DNA Diagnostic Test, *Genome Research* (1998) vol. 8, pp. 549–556.

Chen, Xiangning et al., Fluorescence Energy Transfer Detection As A Homogeneous DNA Diagnostic Method, *Proc. Natl. Acad. Sci. USA,* Sep., 1997, vol. 94, pp. 10756–10761.

Glazer, Alexander N. and Mathies, Richard A., Energy–Transfer Fluorescent Reagents For DNA Analyses, *Analytical Biotechnology,* (1997) vol. 8, No. 1, pp. 94–102.

Hung, Su–Chun et al., Cyanine Dyes With High Absorption Cross Section As Donor Chromophores In Energy Transfer Primers, *Analytical Biochemistry* (1996) vol. 243, pp. 15–27.

Hung, Su–Chun et al., Optimization Of Spectroscopic And Electrophoretic Properties Of Energy Transfer Primers, *Analytical Biochemistry,* (1997) vol. 252, pp. 78–88.

Hung, Su–Chun et al., Comparison Of Fluorescence Energy Transfer Primers, *Analytical Biochemistry* (1998) vol. 255, pp. 32–38.

Innis, Michael A. et al., DNA Sequencing With Thermus Aquaticus DNA Polymerase And Direct Sequencing Of Polymerase Chain Reaction–Amplified DNA, *Proc. Natl. Acad. Sci. USA,* Dec., 1988, vol. 85, pp. 9436–9440.

Ju, Jingyue et al., Energy Transfer Primers: A New Fluorescence Labeling Paradigm For DNA Sequencing And Analysis, *Nature Medicine* Feb., 1996, vol. 2, No. 2, pp. 246–249.

Ju, Jingyue, et al., Cassette Labeling For Facile Construction Of Energy Transfer Fluorescent Primers, *Nucleic Acids Research,* (1996) vol. 24, No. 6, pp. 1144–1148.

Ju, Jingyue et al., Design and Synthesis of Fluorescence Energy Transfer Dye–Labeled Primers and Their Application for DNA Sequencing and Analysis, *Analytical Biochemistry,* (1995) vol. 231, pp. 131–140.

Lee, Linda G.; Connell, Charles R. and Bloch, Will; Allelic Discrimination By Nick–translation PCR With Fluorogenic Probes, *Nucleic Acids Research,* (1993) vol. 21, No. 16, pp. 3761–3766.

Levedakou, Eleni, N.; Landegren, Ulf and Hood, Leroy E.; A Strategy To Study Gene Polymorphism By Direct Sequence Analysis Of Cosmid Clones And Amplified Genomic DNA, *Bio Techniques,* (1989) vol. 7, No. 5, pp. 438–442.

Mead, D. A. et al., Bst DNA Polymerase Permits Rapid Sequence Analysis From Nanogram Amounts Of Template, *Bio Techniques,* (1991) vol. 11, No. 1, pp. 76–87.

Prober, James M. et al., A System For Rapid DNA Sequencing With Fluorescent Chain–Terminating Dideoxynucleotides, *Science,* Oct. 16, 1987, vol. 238, pp. 336–341.

Risch, Neil and Merikangas, Kathleen; The Future Of Genetic Studies Of Complex Human Diseases, *Science,* Sep. 13, 1996, vol. 273, pp. 1516–1517.

Sanger, F., Nicklen, S. and Coulson, A. R.; DNA Sequencing With Chain–Terminating Inhibitors, *Proc. Natl. Acad. Sci. USA,* Dec., 1977, vol. 74, No. 12, pp. 5463–5467.

Wang, Yiwen et al., Microsatellite–based Cancer Detection Using Capillary Array Electrophoresis And Energy–transfer Fluorescent Primers, *Electrophoresis* (1997) vol. 18, pp. 1742–1749.

Wegmuller, B.; Luthy, J. and Candrian, U.; 3'–5' Proofreading–Induced Detection Of Point Mutations By PCR Using Tli DNA Polymerase, *Nucleic Acids Research,* (1995) vol. 23, No. 2, pp. 311–312.

Yu, Hongrun et al., Idenification Of Human Plasma Kallikrein Gene Polymorphisms and Evaluation Of Their Role In End–Stage Renal Disease, *Hypertension* (1998) vol. 31, pp. 906–911.

* cited by examiner

TRI-ALLELIC VARIANT SITE
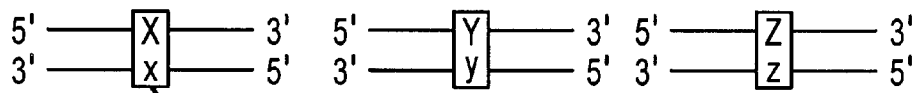
DENATURATION
PRIMER ANNEALING
PRIMER EXTENSION
($ddX^1TP, ddY^2TP, dZ^3TP,$
POLYMERASE)
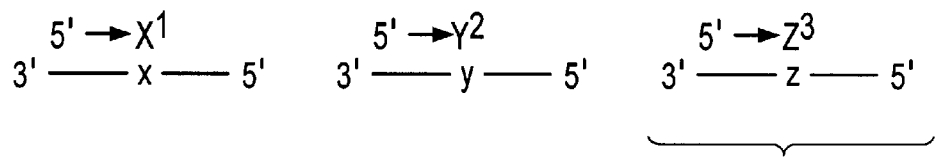
$5' \rightarrow (Z^3)n$
OR
$5' \rightarrow (Z^3)nX^1$
OR
$5' \rightarrow (Z^3)nY^2$
(N IS EQUAL TO OR
GREATER THAN 1)
FIG.2

SNP SCORING
ALLELE I 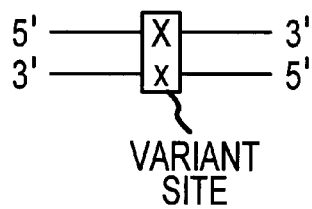
VARIANT SITE
OTHER ALLELES 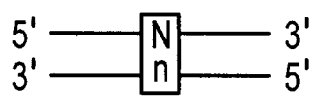
DENATURATION
PRIMER ANNEALING
PRIMER EXTENSION
($ddX^1TP$, 3 dNTPs, POLYMERASE)
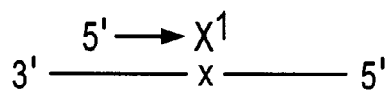
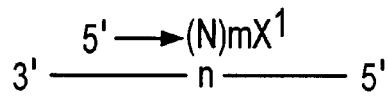
-m IS EQUAL TO OR GREATER THAN 1
-N NUCLEOTIDES DIFFER FROM
  NUCLEOTIDE $X^1$
-$ddX^1TP$ IS LABELED/MODIFIED
FIG.4

5' cttccgtgga gtcttgcagg ggtatcaccc aggagccagg
ctcactgacg ccctcccct ccccacaggc cgccgtgcat
gcctcgggga gccctggcc cgcatggagc tcttc*ctctt*
*cttcacctcc ctgctgc*agc acttcagctt ctcggtgccc
actggacagc cccggcccag ccaccatgg<u>t gtctttgctt</u>
<u>tcctggtga</u>S cccatcccc tatgagcttt gtgctgtgcc
*ccgctagaat ggggtaccta gtccc*cagcc tgctccctag
ccagaggctc taatgtacaa taaagcaatg tggtagttcc
aactcgggtc ccctgctcac gccctcgttg ggatcatcct
cctcaggca accccacccc tgcctcattc ctgcttaccc
caccgcctgg ccgcatttga gacaggggta cgttgaggct
gag 3'

FIG.5

DETERMINATION OF NUCLEOTIDE SEQUENCE VARIATIONS THROUGH LIMITED PRIMER EXTENSION

FIELD OF THE INVENTION

The present invention relates to the field of molecular genetics, including the identification and detection of certain nucleotide sequences.

BACKGROUND OF THE INVENTION

The nucleic acids comprising the genome of an organism contain the genetic information for that organism. The translation or expression of these nucleic acids generates proteins that function in many diverse ways within the organism. Even minute changes in a nucleotide sequence, including single base pair substitutions, can have a siginificant effect in the quality or quantity of a protein. Single nucleotide changes are referred to as single nucleotide polymorphisms or simply SNPs, and the site at which the SNP occurs is typically referred to as a polymorphic site.

Many SNPs, as well as larger nucleic acid alterations, can affect the phenotype of the organism, and in some instances can result in the onset of disease. For example, diseases associated with SNPs include: sickle cell anemia, β-thalassemias, diabetes, cystic fibrosis, hyperlipoproteinemia, a wide variety of autoimmune diseases, and the formation of oncogenes. In addition to causing or affecting disease states, point mutations can cause altered pathogenicity and resistance to therapeutics that target certain microorganisms.

The ability to detect specific nucleotide alterations or mutations in DNA sequences has a number of medical and non-medical utilities. For example, methods capable of identifying nucleotide alterations provide a means for screening and diagnosing many common diseases that are associated with SNPs. Methods that can quickly identify such changes or mutations are also valuable in taking prophylactic measures, assessing the propensity for disease, and in patient counseling and education. As for non-medical applications, such methods have value in the detection of microorganisms, resolving paternity disputes and in forensic analysis to identify perpetrators of crimes.

Various methods have been developed to obtain sequence information for variant sites. Such methods include hybridization reactions between a target nucleic acid and allele-specific oligonucleotidc (ASO) probes (see, e.g., European Patent Publications EP-237362 and EP-32931 1), allele specific amplification (see, e.g., U.S. Pat. Nos. 5,521,301; 5,639,611; and 5,981,176), mini-sequencing methods, quantitative RT-PCR methods (eg., the so-called "TaqMan assays"; see, e.g., U.S. Pat. No. 5,210,015 to Gelfand, U.S. Pat. No. 5,538,848 to Livak, et al., and U.S. Pat. No. 5,863,736 to Haaland, as well as Heid, C.A., et al. *Genome Research*, 6:986–994 (1996); Gibson, U .E. M, et al., *Genome Research* 6:995–1001 (1996); Holland, P. M., et al. *Proc. Natl. Acad. Sci. USA* 88:7276–7280, (1991); and Livak, K. J., et al., *PCR Methods and Applications* 357–362 (1995)), and various single base pair extension (SBPE) assays and related extension assays.

Extension assays typically involve hybridizing a primer that is complementary to a target nucleic acid such that the 3' end of the primer is immediately 5' of the variant site or is adjacent thereto. Extension is conducted in the presence of one or more labeled non-extendible nucleotides that are complementary to the nucleotide(s) that occupy the variant site and a polymerase. The non-extendible nucleotide is a nucleotide analog that prevents further extension by the polymerase once incorporated into the primer. If the added non-extendible nucleotide(s) is(are) complementary to the nucleotide at the variant site, then a labeled non-extendible nucleotide is incorporated onto the 3' end of the primer to generate a labeled extension product. Hence, extended primers provide an indication of which nucleotide is present at the variant site of a target nucleic acid. Such methods are discussed, for example, in U.S. Pat. Nos. 5,846,710; 6,004, 744; 5,888,819; 5,856,092; 5,710,028; and 6,013,431; and in PCT publication WO 92/16657, each of which is incorporated by reference.

Certain SBPE extension reactions suffer from various shortcomings. Some methods generate labeled extension product for only one of the two or more allelic forms of a target nucleic acid. This can be problematic as one cannot distinguish with certainty a failed experiment from the situation in which a sample does not contain a particular allelic form of a target nucleic acid. Often, the extension methods also generate extension products of the same size for different allelic forms of a target nucleic acid. Consequently, different alleles are frequently only distinguished based upon differences in how extension products generated from different allelic forms of the target nucleic acid are labeled (e.g., different extension products bear different labels, or one extension product is labeled whereas another extension product is unlabeled). This means that different allelic forms can be distinguished only by a single criterion.

SUMMARY OF THE INVENTION

The present invention provides methods and kits for detecting and identifying the nucleotide present at the variant site of a target nucleic acid of interest. The methods and kits can be utilized in research, clinical and laboratory settings. In general, the methods involve conducting extension reactions in the presence of a mixture of labeled extendible and labeled non-extendible nucleotides. The detection of incorporation of labeled nucleotide provides an indication of the identity of the nucleotide at the variant site since the incorporated nucleotide is complementary to the nucleotide at the site of variation. The methods can be used in conducting genotyping analyses and can be performed in multiplexing fonnats. The methods and kits have utility in diverse applications including, for example, analyzing point mutations and single nucleotide polymorphisms, detection of pathogens, paternity disputes, prenatal testing and forensic investigations.

Certain methods of the invention are methods of analyzing a variant site of a target nucleic acid and involve conducting a template-dependent extension reaction comprising extending a primer in the presence of the target nucleic acid and a mixture of labeled nucleotides comprising at least one labeled extendible nucleotide and at least one labeled non-extendible nucleotide, each complementary to a different allelic form of the target nucleic acid. The primer hybridizes to a segment of the target nucleic acid such that the 3'-end of the primer hybridizes adjacent the variant site of the target nucleic acid. If the labeled extendible nucleotide is complementary to the nucleotide occupying the variant site, the primer is extended by incorporation of the labeled extendible nucleotide. Whereas, if the labeled non-extendible nucleotide is complementary to the nucleotide occupying the variant site, the primer is extended by incorporation of the labeled non-extendible nucleotide. Incorporation of labeled nucleotide into the extended primer is then detected, with the identity of the labeled nucleotide incorporated into the primer indicating the identity of the nucleotide at the variant site. In some instances, the variant site is a bi-allelic site and the mixture contains a single labeled extendible nucleotide and a single labeled non-extendible nucleotide such as a dideoxynucleotide or an arabinoside triphosphate.

The invention further provides multiplexing methods in which multiple variant sites are analyzed at the same time. Certain of these methods involve conducting a plurality of template-dependent extension reactions in the presence of a plurality of different primers, wherein different primers hybridize adjacent to different variant sites of one or more target nucleic acids and are differentially labeled. Each extension reaction comprises contacting a sample containing the target nucleic acids with multiple copies of one of the different primers, wherein the primer bears a label and the 3'-end of the primer hybridizes adjacent to but not including the variant site of one of the target nucleic acids. The copies of the primer are then exposed to a mixture of nucleotides comprising at least one labeled extendible nucleotide and at least one labeled non-extendible nucleotide under conditions whereby if the labeled extendible nucleotide is complementary to the nucleotide occupying the variant site, at least one copy of the primer is extended by incorporation of labeled extendible nucleotide, whereas if the labeled non-extendible nucleotide is complementary to the nucleotide occupying the variant site, at least one copy of the primer is extended by incorporation of labeled non-extendible nucleotide. Collectively, the extension reactions generate a plurality of different extension products, extension products generated from different variant sites being distinguishable on the basis of the different labels borne by the extended primers. The incorporation of labeled nucleotides into the extension products is detected as an indication of the nucleotides occupying the site of variation in the target nucleic acids.

Kits for conducting certain methods of the invention are also provided by the invention. Some kits include a mixture of nucleotides comprising at least one labeled extendible nucleotide and at least one labeled non-extendible nucleotide, the nucleotides complementary to different allelic forms of a target nucleic acid. Also included is at least one primer, each primer hybridizing to a segment of the target nucleic acid such that the 3' end of the primer is adjacent the variant site of the target nucleic acid. In some instances the primers and labeled nucleotides are selected for use with a SNP that is correlated with a particular disease.

BRIEF DESCRIPTION OF THE DRAWINGS

FIG. 2 illustrates an example of certain methods of the invention for analyzing target nucleic acids having three allelic forms.

FIG. 4 illustrates an example of how certain methods of the invention can be utilized to score the presence or absence of a particular allelic form of a target nucleic acid.

FIG. 5 shows the sequence of the amplimer containing the CYP4.2D6. G4268C SNP (a G/C polymorphic site) (SEQ ID NO:1) (Sachse et al. Am. *J. Hum. Genet.* 60: 284–295 (1997)). The SNP site is indicated by the boldfaced "S" indicating that the variant site is occupied by G or C. The forward and reverse PCR primer binding sites are in bold type and the binding site for the detection primer is underlined.

DETAILED DESCRIPTION

I. Definitions

Figure 1A:
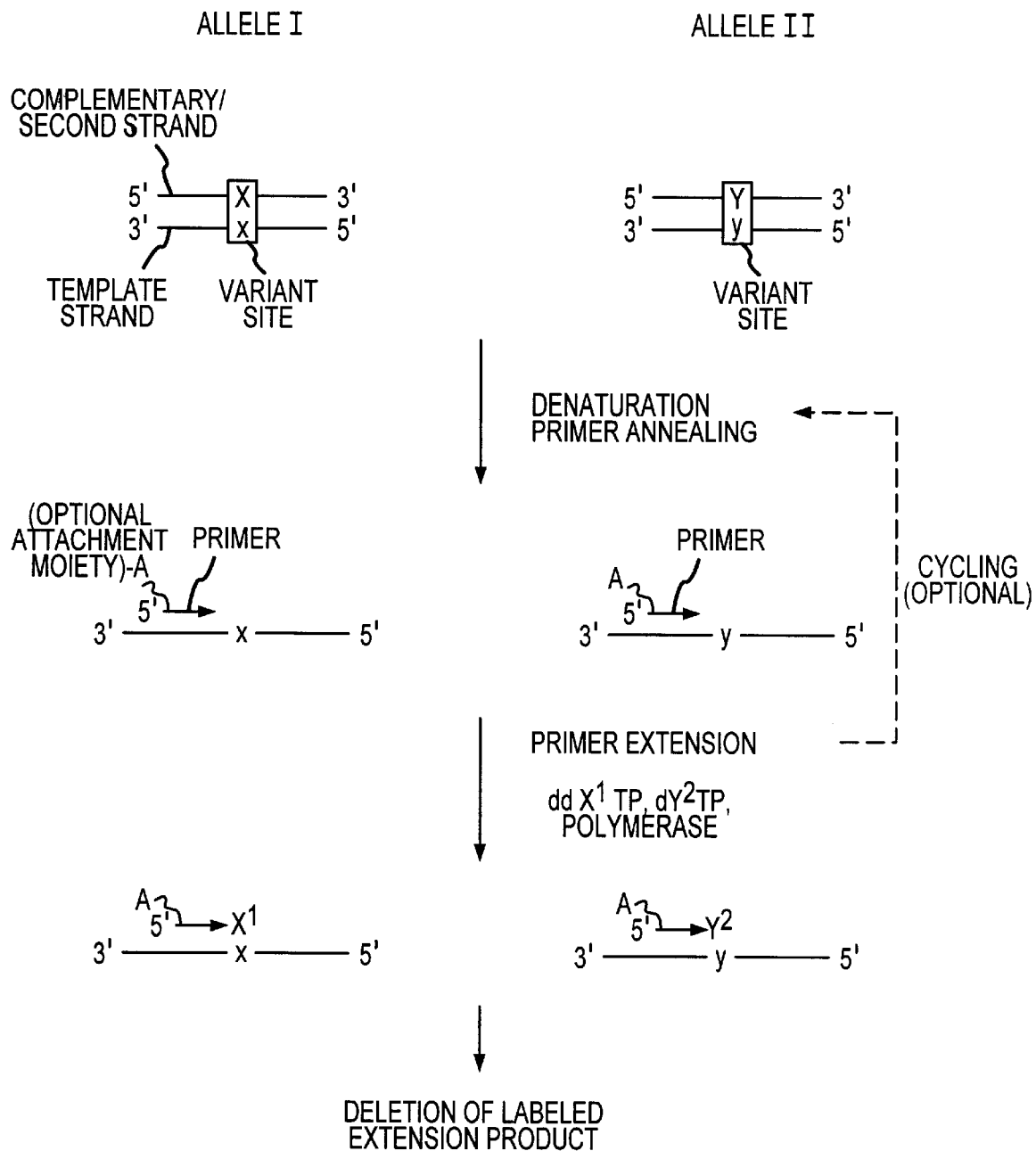
FIG. 1A illustrates the major steps of certain extension methods of the present invention.

A "nucleic acid" is a deoxyribonucleotide or ribonucleotide polymer in either single or double-stranded form, including known analogs of natural nucleotides unless otherwise indicated.

A "polynucleotide" refers to a single- or double-stranded polymer of deoxyribonucleotide or ribonucleotide bases.

An "oligonucleotide" is a single-stranded nucleic acid typically ranging in length from 2 to about 500 bases. Oligonucleotides are often synthetic but can also be produced from naturally occurring polynucleotides. Oligonucleotides can be prepared by any suitable method, including, for example, cloning and restriction of appropriate sequences and direct chemical synthesis by a method such as the phosphotriester method of Narang el al., *Meth. Enzymol.* 68:90–99 (1979); the phosphodiester method of Brown et al., *Meth. Enzymol.* 68:109–151 (1979); the diethylphosphoramidite method of Beaucage et al., *Tetrahedron Lett.* 22:1859–1862 (1981); and the solid support method described in U.S. Pat. No. 4,458,066.

A "primer" is a single-stranded oligonucleotide capable of acting as a point of initiation of template-directed DNA synthesis under appropriate conditions (i.e., in the presence of four different nucleoside triphosphates and an agent for polymerization, Such as, DNA or RNA polymcrase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

A primer that is "perfectly complementary" has a sequence fully complementary across the entire length of the primer and has no mismatches. The priner is typically perfectly complementary to a portion (subsequence) of a target sequence. A "mismatch" refers to a site at which the nucleotide in the primer and the nucleotide in the target nucleic acid with which it is aligned are not complementary.

The term "substantially complementary" means that a primer is not perfectly complementary to its target sequence; instead, the primer is only sufficiently complementary to hybridize selectively to its respective strand at the desired primer-binding site. Selectivity of hybridization exists when hybridization occurs that is more selective than total lack of specificity. Typically, selective hybridization occurs when there is at least 55% identity over a stretch of at least 14–25 nucleotides, preferably at least 65%, more preferably at least 75%, and most preferably at least 90%. Preferably, one ntucleic acid hybridizes specifically to the other nucleic acid. See M. Kanchisa, *Nucleic Acicls Res.*, 12:203 (1984).

Hybridizations are usually performed under stringent conditions that allow for specific binding between an oligonucleotide and a target nucleic acid. A stringent condition is any suitable buffer concentration and temperature that allow specific hybridization of the oligonucleotide to a complementary nuieleic acid. The phrase "hybridizing specifically to" and related phrases, refers to the binding, duplexing, or hybridizing of a molecule only to a particular nucleotide sequence under stringent conditions when that sequence is present in a complex mixture. See M. Kanehisa, *Nucleic Acids Res.*, 12:203 (1984). Strinnent conditions are sequence-dependent and will be different in different circumstances. Longer sequences hybridize specifically at higoler temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the oligonucleotides complementary to the target sequence hybridize to the target sequence at equilibrium. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short oligonucleotides (e.g., 10 to 50 nucleotides) and at least about 60 °C. for longer probes (e.g., greater than 50 nucleotides). Stringent conditions can also be achieved with the addition of destabilizing agents such as formamide.

A "site of variation" or "variant site" when used with reference to a nucleic acid broadly refers to a site wherein the identity of nucleotide at the site varies between nucleic acids that otherwise have similar sequences. For double-stranded nucleic acids, the variant site includes the variable nucleotide on one strand and the complementary nueleotide on the other strand. A variant site can be the site of a single nucleotide polymorphism or the site of a somatic mutation, including a point mutation, a deletion, an insertion, and a rearrangement, for example.

A "polymorphic marker" or "polymorphic site" is the locus at which divergence occurs. Preferred markers have at least two alleles, each occurring at frequency of greater than 1%, and more preferably greater than 10% or 20% of a selected population. The first identified allelic form is arbitrarily designated as the reference form and other allelic forms are designated as alternative or variant alleles. The allelic form occurring most frequently in a selected population is sometimes referred to as the wild-type form, whereas allelic forms occurring less frequently are referred to as mutant alleles. Diploid organisms may be homozygous or heterozygous for allelic forms. A diallelic polymorphism has two forms, a tri-allelic polymorphism has three forms and a tetra-allelic polymorphism has four forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

The term "naturally occurring" as applied to an object means that the object can be found in nature.

The term "subject" and "individual" are used interchangeably herein to refer to any type of organism, but most typically is used to refer to a human.

II. Overview

The present invention provides methods and kits for determining the identity of a nucleotide present at the variant site of a target nucleic acid. The methods involve conducting primer extension reactions in the presence of a mixture of one or more labeled extendible nucleotides and one or more labeled non-extendible nucleotides (e.g., dideoxynuclcotides) to generate labeled primer extension products that are characteristic of the nucleotide occupying the variant site of the target nucleic acid. Depending upon the nature of the sequence downstream of the variant site and the identity of the extendible nucleotide present in the reaction, in some instances the methods generate extension products of differing size for the different allelic forms of the target nucleic acid. Thus, through judicious selection of the particular labeled nucleotides and the use of differentially labeled nucleotides, the methods can in some instances distinguish between allelic forms according to two criteria, namely size and label identity. Because the methods can be designed to generate labeled extension products for all allelic forms of a target nucleic acid of interest, the misinterpretation of negative results which is a shortcoming of other methods can be reduced (e.g., confusing lack of extension product with absence of an allelic form in the sample when lack of product is actually due to a failed experiment). The methods of the invention also allow for high sample throughput.

The general methods of the invention can be adapted to multiplex formats in which the identity of multiple nucleotides at different variant sites is interrogated in a single reaction. Such methods can be performed by using differentially labeled primers for the different variant sites being investigated. Thus, for example, the methods of the invention can be used to determine the identity of the nucleotide at multiple different variant sites on a single or multiple target nucleic acids.

The methods can be used in a number of different applications. For example, in the medical field, the methods of the invention can be used to determine which allele is present at a single nucleotide polymorphic (SNP) site or to detect mutations at a particular site. Because many diseases are associated with SNPs or mutations, the methods can be used in a variety of diagnostic, research and prognostic applications. In addition, for diploid subjects, the methods can be used to determine if the individual is homozygous or heterozygous for a particular allele, i.e., to determine the genotype of the individual. This is an important capability because individuals that are homozygous for an allele associated with a disease are at greater risk than individuals that are heterozygous or homozygous for the allele that is not linked to the disease. Furthermore, individuals that are homozygous for an allele associated with a particular disease sometimes suffer the symptoms of the disease to a greater extent than heterozygotes. The ability of the methods to interrogate particular sites also finds value for identification purposes, including for example, in resolving forensic and paternity cases. The methods also have utility in detecting the presence of nucleic acids from particular pathogens (e.g. certain viruses, bacteria or fungi).

III. Determination of Nucleotide at Variant Site

A. Method Generally

Certain methods of the invention generally involve conducting primer extension reactions in which a target nucleic acid of interest is utilized as a template. The term "target nucleic acid" as used herein refers to single- or double-stranded nucleic acids that include at least one of the variant sites being interrogated. For double-stranded nucleic acids, the variant site includes the nucleotide at the site being examined and the complementary nucleotide in the complementary strand. If a double-stranded target nucleic acid is denatured to form two single strands, each strand can be considered a target nucleic acid and either strand can serve as a template in the methods of the invention. The primer is designed so that once the primer has annealed to the target nucleic acid, its 3'-end is positioned 5' and adjacent to the variant site of the target nucleic acid.

The extension reactions are conducted in the presence of a nucleotide mixture that includes at least one labeled extendible nucleotide and at least one labeled non-extendible nucleotide, as well as a polymerase that catalyzes the incorporation of one or more labeled nucleotides onto the 3'-end of the primer. The labeled nucleotides are typically selected to be complementary to the different nucleotides potentially occupying the variant site of the template strand of the target nucleic acid. If the labeled extendible nucleotide present in the mixture is complementary to the nucleotide occupying the variant site being interrogated, then at least one primer annealed to target nucleic acid within the extension reaction is extended to produce labeled extension product. If a labeled non-extendible nucleotide added to the extension reaction is complementary to the nucleotide at the variant site, then the labeled non-extendible nucleotide is incorporated to produce a different extension product. Since the labeled nucleotide incorporated into the primer is complementary to the nucleotide at the variant site of the template, by determining which labeled nucleotide is incorporated into the primer, one can identify the nucleotide present at the variant site.

As used within the context of the primer extension reaction, the term "nucleotide" refers to any of the naturally occurring deoxynucleotides (i.e., dATP, dTTP, dGTP and dCTP), dideoxynucleotides, or derivatives of the foregoing, so long as the nucleotide can be incorporated at the 3'-end of a primer during template-dependent primer extension. Hence, a nucleotide can be an extendible nucleotide and/or a non-extendible nucleotide. An "extendible nucleotide" refers to nucleotides to which another nucleotide can be attached at the 3' position of the ribose moiety. Thus, extendible nucleotides include the naturally occurring deoxynucleotides dATP, dTTP, dCTP and dGTP, as well as derivatives of these nucleotides that are extendible.

A "non-extendible nucleotide" refers to nucleotide analogs that once incorporated into the primer cannot be extended further, i.e., there is no 3' hydroxyl group or the 3' hydroxyl group has been modified such that another nucleotide cannot be attached at the 3' position. Thus, suitable non-extendible nucleotides include nucleotides in which the 3' hydroxyl group is substituted with a different moiety such that another nucleotide cannot be joined to a primer once the non-extendible nucleotide is incorporated into the primer. Such moieties include, but are not limited to, —H, —SH and other substituent groups. Specific examples of non-extendible nucleotides include dideoxynucleotides and arabinoside triphosphates.

Each of the nucleotides contacted with the target nucleic acid include labeled forms. The term "labeled" when used in reference to the nucleotides utilized in conducting the extension reaction or a reference to a nucleotide bearing or being attached to a label means that the nucleotides bear a detectable label (see infra) or are modified/derivatized to permit labeling of the nucleotide following the extension reaction. If the nucleotides are modified, different nucleotides can be modified in different ways to allow for selective differential labeling of different nucleotides. For example, different nucleotides can be derivatized to bear different functional groups that selectively react with a certain functional group associated with a particular label.

As indicated above, the nucleotide mixture utilized in the extension reactions generally include at least one labeled extendible nucleotide and at least one labeled non-extendible nucleotide. Specific analyses, however, can be configured in a variety of different formats. The following list provides specific examples of certain combinations of extendible and non-extendible nucleotides that can be utilized:

| 1 dNTP, 1 ddNTP | 2 dNTP, 1 ddNTP | 3 dNTP, 1 ddNTP |
| 1 dNTP, 2 ddNTP | 2 dNTP, 2 ddNTP | 3 dNTP, 2 ddNTP |
| 1 dNTP, 3 ddNTP | 2 dNTP, 3 ddNTP | 3 dNTP, 3 ddNTP |
| 1 dNTP, 4 ddNTP | 2 dNTP, 4 ddNTP | 3 dNTP, 4 ddNTP |

Often the analysis is of a biallelic variant site. Some analyses of such sites utilize a single labeled non-extendible nucleotide in combination with a single labeled extendible nucleotide. For tri-allelic and tetra-allelic variant sites, in certain methods, the number of non-extendible nucleotides is increased to two and three, respectively (see infra).

B. Strand Separation and Annealing

1. Strand separation

The various major steps of certain methods of the invention are illustrated in FIG. 1A, which illustrates a method for analyzing a target nucleic acid that has two allelic forms (e.g., a biallelic SNP). The same general steps, however, apply to target nucleic acids having more allelic forms (see FIGS. 2–4). The letters W/w; X/x; Y/y and Z/z are used in FIGS. 1A–4 to represent any of the standard deoxynucleotides (i.e., A, T, G or C), with different letters representing different nucleotides. The lower case letters represent the nucleotide at the variant site on one strand of the target nucleic acid and the upper case letter represents the complementary nucleotide on the complementary strand. Thus, W/w represent complementary bases on opposite strands of a target nucleic acid, as do X/x, Y/y and Z/z. The arrows in the figure represent primers.

The methods of the invention begin with the treatment of a sample that includes a duplex target nucleic acid to obtain unpaired nucleotides that at least span the variant site of interest or, alternatively, to obtain separate strands. Of course, if the target nucleic acid is already single-stranded, such a step is unnecessary. Strand separation can be achieved using various denaturing conditions that are known in the art including, for example, heat, alkali, formamide, urea, glyoxal and combinations thereof. Typically, strand separation is achieved using heat denaturation at temperatures ranging from 80 °C. to about 105 °C. for time periods ranging from about 1 to 10 minutes. Alternatively, single-stranded template can be generated through degradation of one strand of a duplex by exonucleases (see, eg., Somers et al, *Biochimica et Biophysicia Acta* 1379: 42–52 (1998); Nikiforov et al., *PCR Methods and Applications* 3: 285–291 (1994); Higuchi and Ochman, *Nucleic Acids Research* 17: 5865 (1989); and Straus and Zagursky, *Biotechniques* 10: 376–384 (1991)).

2. Annealing

A primer (also referred to as a detection primer) is annealed under hybridizing conditions to a single-stranded target nucleic acid/ template strand formed during denaturation. The primer specifically hybridizes to a segment of the target nucleic acid such that its 3' end is adjacent to the variant site on the target nucleic acid (see FIG. 1A). As used herein, the term "adjacent" when used in reference to hybridization between the primer and target nucleic acid typically means that the primer hybridizes to the target nucleic acid so that its 3' end is immediately 5' to the variant site. However, the 3' end can be located several nucleotides 5' to the variant site so long as none of the nucleotides between the 3' end of the primer and the variant site are the same as the nucleotide that potentially occupies the variant site.

3. Primers

A variety of different types of primers can be utilized with the present methods. Suitable primers include, for example, an oligodeoxyribonucleotide, an oligoribonucleotide, a peptide nucleic acid or a copolymer thereof. Primers can be either naturally occurring nucleic acids or prepared using synthetic methods. If synthesized, the primers can be synthesized either enzymatically in vitro, enzymatically in vivo or non-enzymatically in vitro.

Depending upon the nature of the target nucleic acid (see section on samples infra) various combinations of primer/target nucleic acid duplexes can be formed. For example, in some methods the template is a deoxyribonucleic acid and the primer is an oligodeoxyribonucleotide, an oligoribonucleotide, or a copolymer thereof. In such instances, a DNA polymerase is utilized to generate a DNA product. In certain other methods, the template is a ribonucleic acid and the primer is an oligodeoxyribonucleotide, an oligoribonucleotide, or a copolymer thereof. Reverse transcriptase can be utilized to form a DNA product. In yet other methods, the template is a deoxyribonucleic acid and the primer is an oligoribonucleotide. Added RNA polymerase can produce an RNA product from such a duplex. Finally, if the template is a ribonucleic acid and the primer an oligoribonucleotide, then an RNA replicase can form an RNA product.

Primers are sufficiently long to specifically hybridize to the appropriate target nucleic acid and to form a stable hybridization complex under the extension reaction conditions. Typically, the primers are 15 to 50 nucleotides in length; in other instances, the primers are 20 to 30 nucleotides long. The length of the primers can be adjusted to be longer or somewhat shorter depending upon the particular sequence to whiclh a primer hybridizes (e.g., primers with a high G/C content typically can be shorter than those with a low G/C content). Most typically, the primers are designed to be perfectly complementary over their entire length with the template strand. However, in certain methods the primers are substantially complementary to the target nucleic acid; mismatches in such instances, however, should not adversely affect the stability of the primer/target nucleic acid hybridization complex.

In certain methods, the primer can include one or more moieties that allow for the affinity separation of the extension product from unincorporated reagents and/or target nucleic acid and/or other nucleic acids in the test sample. Such attachment moieties are described further infra in the section on detection. Additionally, the primer can include a label to facilitate detection of extended primer. Alternatively, the primer can include a modified nucleotide that facilitates selective labeling following the extension reaction. Hence, the term "label" when used in reference to label borne by a primer or the term "labeled primer" or reference to a primer bearing a label includes primer that actually bears a label, as well as primers that include modified nucleotides for attachment of label subsequent to extension reactions. Suitable labels can be selected from those described below in the section on labeled nucleotides.

C. Extension

With continued reference to FIG. 1A, the duplex including primer and target nucleic acid is contacted with the mixture of labeled nucleotides and a polymerase to initiate extension of the primer. As noted supra, the mixture of nucleotides include at least one labeled extendible nucleotide and at least one labeled non-extendible nucleotide. The labeled nucleotides are selected to be complementary to one of the nucleotides potentially at the variant site of the target nucleic acid under investigation. If an added nucleotide is complementary to the nucleotide at the variant site of the target nucleic acid, then the polymerase catalyzes the incorporation of this nucleotide to generate an extended primer. Since the incorporated nucleotide is complementaiy to the nucleotide occupying the variant site, the incorporated nucleotide provides the basis for identifying the nucleotide at the variant site.

Because primer extension is conducted in the presence of extendible nucleotides, depending on the sequence of the template downstream (ie., in the direction of polymerization on the extension primer) of the variant site, primer extension can extend past the variant site. For example, if one or more nucleotides immediately downstream of the variant site are the same as the nucleotide at the variant site, extension can proceed downstream of the variant site to include these nucleotides when reactions are conducted with extendible nucleotides complementary to the nucleotide at the variant site. Extension beyond the variant site can be advantageous in certain instances because the net result is that different allelic forms generate different sized extension products, thereby providing another criterion for allele discrimination. Hence, if extension reactions are conducted in the presence of differentially labeled nucleotides, in some instances different allelic forms can be distinguished on the basis of the identity of the label incorporated into the extension product and according to the size of the extension product.

Figure 1B:
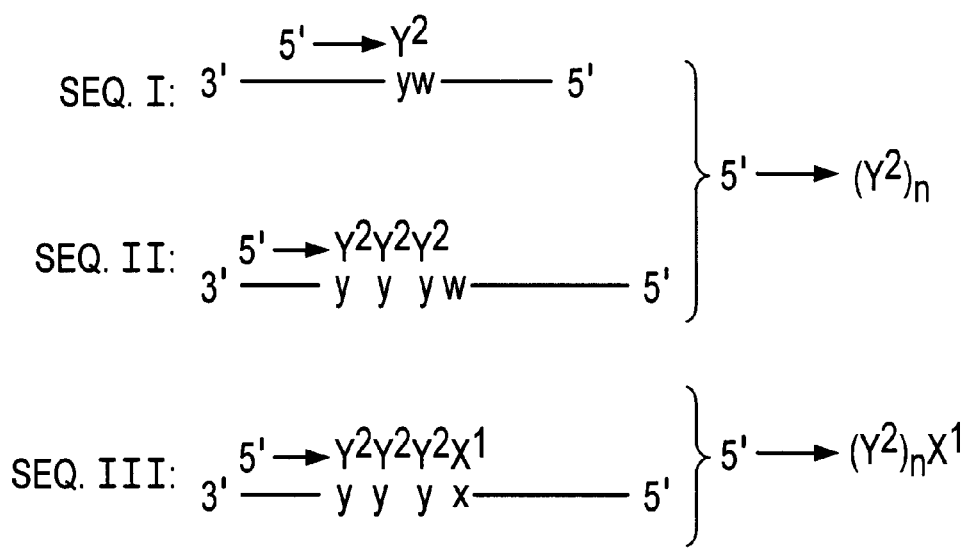
FIG. 1B shows examples of the different sized extension products that can be formed according to certain methods of the invention in which extension reactions are conducted in the presence of a mixture of nucleotides that includes an extendible nucleotide (e.g., a deoxynucleotide) that is complementary to one or more nucleotides located 3' (i.e., downstream) of the variant site such that extension proceeds past the variant site.

Examples of extension products formed in situations in which nucleotides downstream of the variant site are the same as the nucleotide at the variant site are illustrated in FIG. 1B. This figure depicts examples of different extension products that can be generated from allele II shown in FIG. 1A for different exemplary sequences downstream of the variant site. In the case of SEQ I, the nucleotide immediately downstream of the variant site (represented by "w") is a nucleotide that is not complementary to either of the labeled nucleotides ($X^1$ and $Y^2$) present in the reaction mixture. Consequently, extension terminates upon incorporation of nucleotide complementary to the nucleotide present at the variant site. SEQ II and SEQ III, however, illustrate the situation in which one or more nucleotides downstream of the variant site are the same as the nucleotide at the variant site. In such instances, extension continues downstream of the variant site. Extension terminates once a nucleotide that is not complementary to one of the added nucleotides is reached (the case with SEQ II) or when a nucleotide complementary to the non-extendible nucleotide present in the extension reaction mixture is reached (the case with SEQ III).

A variety of techniques can be used to control the extent of the extension reaction when labeled extendible nucleotides are incorporated into the primer. Under appropriate conditions, reactions can be controlled so that only a limited number of deoxynucleotides are incorporated at the variant site, even though the sequence of the template would allow for the incorporation of additional deoxynucleotides. Such techniques include, but are not limited to, controlling polymerase concentration, limiting extension reaction times and conducting extension reactions at low temperatures (e.g., approximately 40° C. to 60° C. with the polymerase Taq FS (Perkin Elmer)). Such control can be useful in controlling extension product size when it is advantageous to discriminate between different allelic forms according to size.

In certain methods, some or each of the labeled nucleotides can be provided as a mixture of labeled and unlabeled forms. The concentration of the unlabeled form for a particular nucleotide relative to the total concentration of labeled and unlabeled forms for that nucleotide is at least 20%, 25%, 30%, 35%, 40%, 45%, 50%, 55% or 60% on a molar basis. The upper limit on the concentration of the unlabeled forms relative to the total amount of both forms is typically 80%, 85%, 90% or 95% on a molar basis. In certain methods, the unlabeled concentration typically is 30% to 95% on a molar basis. In other methods, the unlabeled form is generally 50% to 90% on a molar basis. In still other methods, ratio of unlabeled to labeled forms on a molar basis is 1:2. Although commercially available labeled nucleotides (e.g., TAMRA-ddATP), can sometimes contain relatively low levels of unlabelled forms (generally about 5%), the concentration of unlabeled forms used in the present invention are above such levels and is in accordance with the ranges set forth above. The use of a mixture of labeled and unlabeled forms can be useful in reducing misincorporation of nucleotides into extension products and in regulating signal strength for different extension products. The use of mixtures of labeled and unlabeled forms of nucleotides is described in a copending and commonly owned U.S. patent application having application Ser. No. 09/585,768, which is incorporated by reference in its entirety.

As indicated above, in some instances the 3' end of the primer is several nucleotides 5' of the variant site. The nucleotides of the target nucleic acid in this gap should not include a nuclcotide that potentially occupies the variant site being analyzed. In such a situation, deoxynucleotide triphosphates (dNTPs) complementary to the nuclcotides between the 3' end of the primer and the variant site should be included in the extension reactions.

The timing at which components are added relative to the strand separation, annealing and extension processes just described can vary. For example, reactions can be carried out by first converting the target nucleic acid to fonn single strands, annealing the primer to one of the single strands and then adding the mixture of nucleotides and polymerase. Alternatively, in some methods, target nucleic acid, the mixture of nucleotides and the polymerase are all combined before strand separation and primer annealing.

D. Detection

Extension product formation is detected by detecting the incorporation of label into the primer by various direct or indirect methods (see FIG. 1A). In some instances, extension product is initially separated from unrcacted reactants in the extension reaction mixture before extension product is detected. With certain techniques, however, such separation is unnecessary and the methods can be performed in a homogenous format.

1. Separation Based Methods

Once extension reactions have been completed, in some instances extended primer product is separated from unextended primers and unincorporated labeled nucleotides to facilitate analysis. Following removal of components that might interfere with the detection step, extended primer can be analyzed for presence or absence of label; the particular labeled nucleotide incorporated into the extended primer serving as an indicator of the nucleotide that occupies the variant site.

Separation of the extended primers from other reaction components can be achieved in a variety of ways. In one approach, the primer includes an attachment moiety that is one component of an affinity pair and that allows for affinity purification of extended primer from other components of the extension reaction. Typically, the attachment moiety is located at or near the 5' end of the primer. The other member of the affinity pair is frequently attached to a solid support such that extended primer including the labeled nucleotide can be bound to the support via the attached member of the affinity pair. Other reaction components can then be washed away.

A variety of different attachment moieties can be used as part of an affinity pair to achieve purification of the extended primer from other components. In general terms, the attachment moiety and the other component of the affinity pair include two agents that are capable of specifically binding to one another. Examples of such binding pairs include, but arc not limited to, polynucleotidc/complementary polynucleotide, biotin/avidin, antigen/antibody and heavy metal/thiol group. In some instances, one member of the affinity pair is attached to a solid support. A solution containing (or potentially containing) a primer bearing the complementary member of-the affinity pair is then contacted with the support. After allowing the two components an opportunity to bind and fomi a complex, other species in the extension reaction mixture can be washed from the support.

Thus, by way of example and not limitation, in one suitable arrangement, the attachment moiety is a polynucleotide that serves as a 5' extension to the primer. A complementary nucleotide is attached to a solid support and is capable of selectively binding the extension primer. Alternatively, an antigen functions as the attachment moiety and an antibody specific thereto is attached to the support. In yet another arrangement, a thiol group is linked to the primer and serves as the attachment moiety. A heavy metal group attached to the solid support can be used to selectively bind the thiolated primer.

The attachment moiety can be attached at any point of the primer where it does not interfere with the extension reaction. Most typically the attachment moiety is attached at or near the 5' end of the primer. However, in some instances, the attachment moiety is connected at a more internally located nucleotide.

Instead of attaching the attachment moiety to the primer, in some methods the attachment moiety is part of the nucleotide. The attachment moiety can be selected from the group of affinity pairs described above, for example (see, also, U.S. Pat. No. 5,710,028 to Eyal, et al.). Alternatively, one can obtain antibodies specific to a fluorescent dye label on the nucleotide (e.g., an antibody elicited to fluorescein as a hapten). Such antibodies have been discussed (see Voss, E. W., Jr. (ed) *Fluorescein Hapten: An Immunological Probe*).

A variety of different types of supports can be utilized in methods employing affinity-binding pairs. Suitable supports include, but are not limited to, beads, microparticles, the surface of a microtiter well, a filter and a glass slide. Similarly, the supports can be formed from any material stable to the binding and washing conditions including, for example, glass, polystyrene, cellulose, latex, nitrocellulose, nylon, polyacrylamide, dextran and agarose.

As an alternative to the use of attachment moieties and affinity binding pairs, extended primers can be separated from other reaction components by various size-based methods such as gel electrophoresis and size exclusion chromatography (e.g., HPLC). In some methods, separation of components by gel electrophoresis and the detection step (typically detection of fluorescence from a fluorescent label attached to the extended primer via the incorporated nucleotide) is performed using a single integrated instrument, such as the Prizm DNA Sequencers from Applied Biosystems, and MegaBACE from Molecular Dynamics. Another option that does not require separation is to selectively inactivate the label associated with unincorporated nucleotide.

2. Homogenous Assays

Certain methods are conducted in a hoomogenous assay format in which extension products do not need to be separated from other extension reaction components (e.g., unextended primer and unincorporated nucleotide). In some methods, this is accomplished using donor and acceptor fluorophores, including fluorescence resonance energy transfer pairs. The fluorophores are chosen so that the emission spectrum of one fluorophore (i.e., the donor fluorophore) overlaps the excitation spectrum of the other fluorophore (i.e., the acceptor fluorophore).

With such methods, the labeled nucleotide bears one member of the donor/acceptor dye pair and the other member is attached to the primer. The primer can be labeled at a position such that upon the incorporation of the labeled nucleotide the donor and acceptor are brought into an energy transfer relationship, wherein fluorescence energy can be transferred from the donor to the acceptor. By measuring fluorescence changes that occur as a consequence of energy transfer (e.g., a decrease in the fluorescence intensity of the donor or an increase in the fluorescence intensity of the acceptor), one can detect the incorporation of label onto the primer without having to separate extension product from unreacted reactants. Specific labels suitable for use in such methods are discussed infra in the section on labels. Further guidance on such methods is described in U.S. Pat. No. 5,945,283 and in a copending and commonly owned U.S. patent application having application Ser. No. 09/547,292, which is incorporated by reference in its entirety.

3. Indirect Methods

An alternate detection method is to measure the change in reactant concentration as an indication of which nucleotide is incorporated into a primer during the extension reaction. Fluorescence polarization techniques can be utilized conveniently for this purpose. This technique is able to distinguish between large and small molecules based on molecular tumbling. Large molecules (e.g., labeled extension product) tumble in solution much more slowly than small molecules. Thus, the signal from a labeled nucleotide incorporated into a primer can be distinguished from the labeled nucleotide free in solution (see, e.g., Chen et al., Genome Research 9:492–8 (1999), and U.S. Pat. No. 5,593,867 to Walker et al., both of which are incorporated by reference in their entirety).

4. Labels

Labeled nucleotides either bear a label that is either directly or indirectly detectable or the nucleotide has been modified to allow for selective and rapid labeling at some point prior to detection, typically after the extension reaction A label attached to the nucleotide, and optionally to the primer, can be any compound or molecule that can be detected and that does not significantly interfere with the extension reaction (e.g., interfering sufficiently such that an undetectable amount of extension product is formed and/or causing elevated rates of misincorporation such that an accurate determination of the identity of the nucleotide at the variant site is not possible). Suitable labels include, but are not limited to, fluorophores, chromophores, molecules that emit chemiluminescence, magnetic particles, radioisotopes, mass labels, electron dense particles, electrochemically active molecules, enzymes, cofactors, substrates for enzymes and ligands having specific binding partners (e.g., avidin/biotin). Mass labels can be prepared from various monomers. By joining differing numbers of monomers together, mass labels of differing molecular weight can be prepared. Essentially, any type of monomer that can be joined together and then attached to a primer can be used, so long as the mass label does not interfere with hybridization of the primer to the target nucleic acid.

Certain methods utilize fluorescent molecules as the labels, as a number of commercial instruments have been developed for the detection of fluorescently labeled nucleic acids. A variety of fluorescent molecules can be used as labels including, for example, fluorescein and fluorescein derivatives, rhodamine and rhodamine derivatives, naphthylamine and naphthylamine derivatives, cyanine and cyanine derivatives, benzamidizoles, ethidiums, propidiums, anthracyclines, mithramycins, acridines, actinomycins, merocyanines, coumarins, pyrenes, chrysenes, stilbenes, anthracenes, naphthalenes, salicyclic acids, benz-2-oxa-1-diazoles (also called benzofurazans), fluorescamines and bodipy dyes.

For those methods in which the detection primer and/or the detection product are labeled with fluorescent dyes capable of energy transfer to enhance emission intensities or simplify the assay, a number of donor (or reporter) and an acceptor (or quencher) dyes are available. One group of donor and acceptor dyes includes the xanthene dyes, such as fluorescein dyes, and rhodamine dyes. A variety of derivatives of these dyes are commercially available. Often functional groups are introduced into the phenyl group of these dyes to serve as a linkage site to an oligonucleotide. Another general group of dyes includes the naphthylamines which have an amino group in the alpha or beta position. Dyes of this general type include 1-dimethylaminollaphthyl-5-sulfonate, 1-anilino-8-naphthalene sulfonate and 2-p-toluidinyl-6-naphthalene sulfonate.

Other dyes include 3-pheniyl-7-isocyanatocoumarini, acridines, such as 9-isothiocyanatoacridine and acridine orange, pyrenes, benzoxadiazoles, and stilbenes. Additional dyes include 3 -($\epsilon$-carboxypentyl)-3'-ethyl-5,5'-dimethyloxa-carbocvanine (CYA); 6-carboxy fluorescein (FAM); 5&6-carboxyrhodamine-110 (R110); 6-carboxyrhodamine-6G (R6G); N',N',N',N'-tetranmethyl-6-carboxyrhodaminc (TAMRA); 6-carboxy-X-rhodamine (ROX); 2', 4', 5', 7', - tetrachloro -4-7- dichlorofluorescein (TET); 2', 7'- dimethoxy - 4', 5'- 6 carboxyrhodaninie (JOE); 6-carboxy-2'4,4',5',7,7'-hexachlorofluorescein (HEX); ALEXA; Cy3 and Cy5. These dyes are commercially available from various suppliers such as Applied Biosystems Division of Perkin Elmer Corporation (Foster City, Calif.), Amershamii Phaniacia Biotech (Piscataway, N.J.), and Molecular Probes, Inc. (Eutgene, Oreg.).

Further guidance regarding the selection of donor and acceptor pairs that can effectively be used with the methods of the present invention includes: Fluorescence *Spectroscopy* (Pesce et al., Eds.) Marcel Dekker, New York, (1971); White et al., *Fluorescence Analysis: A Procrtical Approach*, Marcel Del(ker, New York, (1970); Berlman, *Handbook of Fluorescence Spectra of Aromatic Molecules*, $2^{nd}$ ed., Academic Press, New York, (1971); Griffiths, *Colour and Constitution of Organiic Molecules*, Academic Press, New York, (1976); *Indicators* (Bishop, Ed.). Pergamon Press, Oxford, 19723; and Haugland, *Handbook of Fluorescent Probes and Research Chemicals*, Molecular Probes, Eugene (1992).

IV. Tri-Allelic and Tetra-Allelic Variant Sites

A target nucleic acid having a tri-allelic or tetra-allelic variant site includes three and four allelic forms, respectively. Said differently, the number of different nucleotides potentially occupying the variant site is three and four, respectively. The methods for analyzing the variant site of such target nucleic acids generally parallel the methods for analyzing bi-allelic variant sites.

For example, as illustrated in FIG. 2, certain methods for analyzing a target nucleic acid having a tri-allelic variant site involve conducting extension reactions in the presence of two labeled non-extendible nucleotides (ddX$^1$TP, ddY$^2$TP) and one labeled extendible nucleotide (dZ$^3$TP). The nucleotides are selected to be complementary to the nucleotides that potentially occupy the variant site of the template strand (x, y and z, respectively). In such instances, the extendible nucleotide can be complementary to any of the allelic forms. However, if the nucleotide (or nucleotides) downstream to the variant site is (are) the same as one of the nucleotides potentially at the variant site, it can be advantageous to select the extendible nucleotide as the one that is complementary to the nucleotide(s) downstream of the variant site. In such an experimental arrangement, extension of the primer continues downstream of the variant site for each of downstream nucleotides that are the same as the nucleotide located at the variant site. As noted supra, the fonnation of different sized extension products for different alleles can simplify the analysis by allowing different allelic forms to be distinguished on the basis of size in addition to other criteria such as differential labeling.

FIG. 2 illustrates the different types of extension products that can be formed when one or more nucleotides located downstream of the variant site is (are) the same as one of the nucleotides that potentially occupies the variant site and the extendible nucleotide included in the extension reaction mixture is complementary to these nucleotides. In general, extension terminates at the variant site if one of the labeled non-extendible nucleotides included in the reaction mixture is complementary to one of the nucleotides at the variant site (products represented by primer-X$^1$, primer-Y$^2$ and primer-Z$^3$). When, however, the nucleotide at the variant site of the template is complementary to the labeled extendible nucleotide included in the extension reaction, then extension can continue downstream of the variant site, so long as the downstream nucleotides are the same as the nucleotide at the variant site.

Once a nucleotide in the template strand is encountered that differs from the nucleotide at the variant site, extension terminates. If the different nucleotide is complementary to one of the non-extendible nucleotides added, then extension tenninates upon incorporation of the complementary non-extendible nucleotide (such products are represented as primer-(Z$^3$)nX$^1$ or primer-(Z$^3$)nY$^1$ in FIG. 2 (n being equal to or greater than one). If, however, the different nucleotide in the template strand is not complementary to any of the nucleotides present in the extension reaction, then the extension reaction tenninates with incorporation of the extendible nucleotide corresponding to the last nucleotide in the template strand that is the same as the nucleotide at the variant site (this product is represented by primer-(Z$^3$)n in FIG. 2, where n again is equal to or greater than one).

In some instances, continued extension downstream of the variant site can be halted prior to the extended primer reaching the different nuclcotide by utilizing, the techniques described above (e.g., restricted reaction time, low concentrations of polymerase and low temperature). The different extension products can be distinguished according to the different labels borne by the nucleotides and optionally according to size (e.g., allele III in FIG. 2 can generate extension products that differ in size from those generated from alleles I and II).

Figure 3:
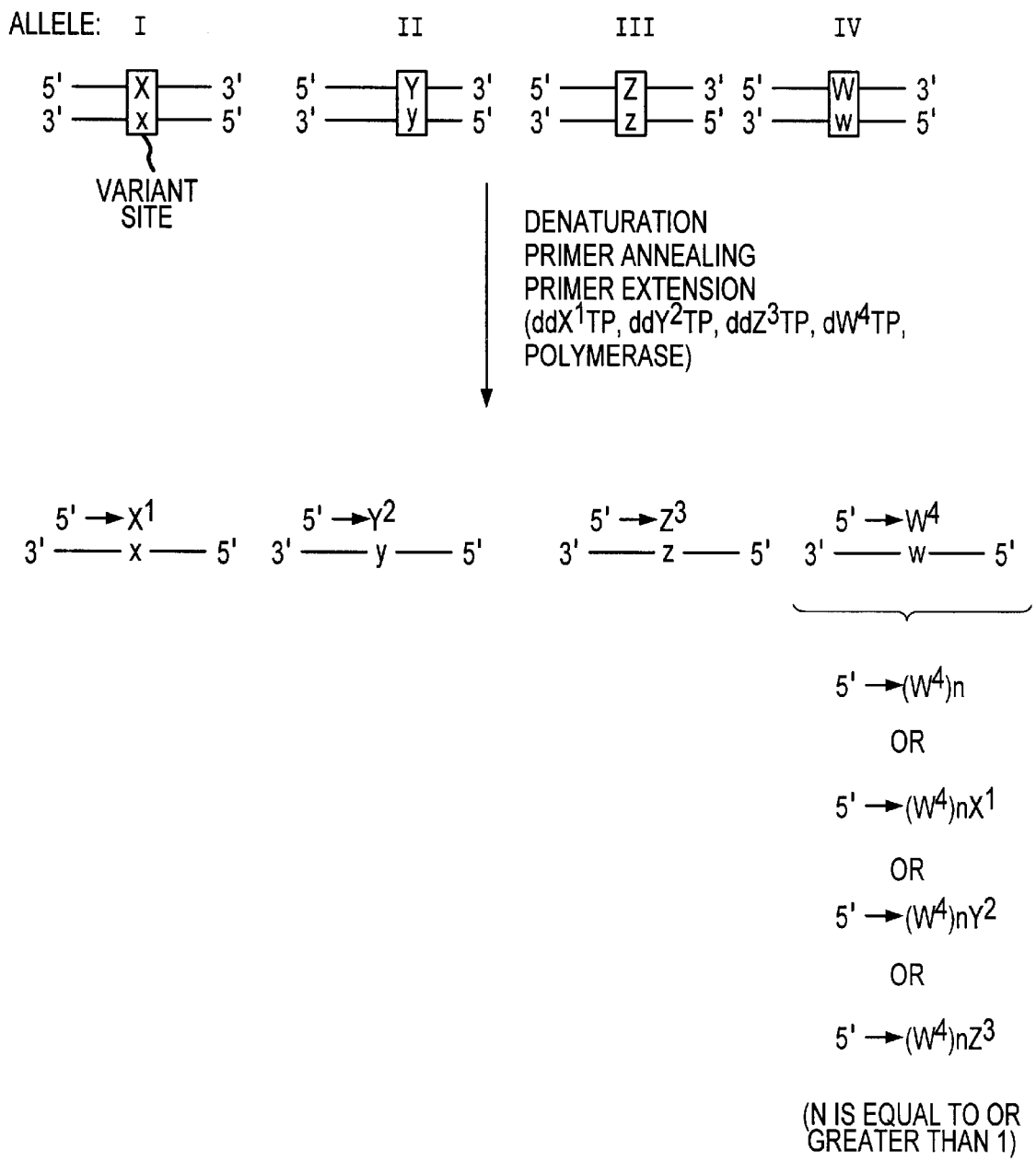
FIG. 3 depicts an example of certain methods of the invention for analyzing, target nucleic acids having four allelic foiis.

A related method for analyzing a nucleic acid having a tetra-allelic variant site is shown in FIG. 3. In one example of a method for analyzing tetra-allelic sites, reactions are conducted with three labeled non-extendiblc nucleotides (ddX$^1$TP, ddY$^2$TP and ddZ$^3$TP) and one labeled extendible nucleotide (dW4TP). As described for the biallelic and tri-allelic situations, extension terminates at the variant site if one of the labeled non-extendible nucleotides included in the extension reaction is complementary to the nucleotide at the variant site (such products are represented by primer-X$^1$, primer-Y$^2$ and primer-Z$^3$ in FIG. 3). If, however, the labeled extendible nucleotide included in the extension reaction is complementary to the nuclcotide at the variant site of the target nucleic acid, then extension can continue downstream of the variant site. In this instance, extension 3' of the variant site terminates upon the incorporation of non-extendible nucleotide. Such products are represented as primer-(W$^4$) nX$^1$, primer-(W$^4$)nY$^2$ and primer-(W$^4$)nZ$^3$, where n is equal to or greater than one. The various products can be distinguished by differential labeling of the different nulceotides and optionally the different sizes of the extension products.

V. Scoring Variant Sites

Certain methods are designed to identify and detect one particular allele, while simultaneously detecting but not specifically identifying the presence of other alleles. Such methods are referred to as scoring a variant site. The general approach for such scoring methods arc illustrated in FIG. 4. Reactions in such methods are typically performed utilizing a single non-extendible nucleotide (ddX$^1$TP) that is complementary to the nucleotide present in the target nucleic acid for the allele of interest (nucleotide x for Allele I) and three extendible nucleotides (dNTPs). Collectively, the extendible nucleotides and non-extendible nucleotide generally are selected to include all four bases (i.e., A, T, G and C).

If the sample includes a copy of the target nucleic acid having the allele of interest (allele I; represented by the nucleotide x), then the primer is extended by incorporation of the non-extendible nucleotide (X). Incorporation of the non-extendible nucleotide terminates the extension reaction and results in the formation of an extension product including the non-extendible nucleotide at the 3'-end (i.e., primer-$X^1$ in FIG. 4). Target nucleic acids that include the other alleles generate extension products that differ in size from extension product corresponding to the allele of interest. In the case of the other alleles, primer is initially extended to incorporate the extendible nucleotide that is complementary to the base occupying the variant site of the template strand. The extension reaction continues until the base corresponding to the allele of interest is reached in the template. At this point, non-extendible nucleotide is incorporated and the extension reaction terminates. Such reaction products are represented in FIG. 4 as primer-(N)mX1, where N stands for nucleotides other than the nucleotide X and m is equal to or greater than 1. Thus, while extension product for the allele of interest is extended by a single nucleotide, other allelic forms of the target nucleic acid generate extension products that are at least one base pair longer than extension product for the allele of interest. Consequently, the allele of interest can be distinguished (i.e., scored) from the other alleles present in a sample by the size of the extension products.

VI. Multiplexing/Pooling

Certain methods of the invention can be extended to multiplexing formats in which the identity of a nucleotide at multiple variant sites is determined in a single reaction. Such formats allow for rapid sequence determinations in many loci and,or individuals simultaneously. The multiple sites can be multiple sites on the same target nucleic acid, such sites being within the same gene or at sites in different genes. Alternatively, the multiple sites can be different sites on target nucleic acids obtained from different individuals.

In certain multiplexed methods, primers for each of the different variant sites are annealed to their respective binding sites. The general structure of the primers and the methods for conducting the extension reactions is as set forth above. Here too, the particular labeled nucleotide(s) incorporated into the extended primer serves to identify the nucleotide(s) present at the variant sites of the target nucleic acids.

In order to correlate the multiple extension products with the various sites, a number of different strategies can be utilized to aid in determining which extension product corresponds with which variant site. One option is to differentially label the nucleotides such that different labels are used for different variant sites. Another approach involves using primers of different lengths so that the extension products formed are of differing sizes and capable of being distinguished by size fractionation (e.g., by gel electrophoresis). If this approach is utilized, the primers can differ by as little as a single nucleotide, although typically the difference in size is larger to facilitate discrimination of the different extension primers.

Alternatively, primers can be tagged with distinctive identifier tags. A number of different tags can be utilized. In some instances, a secondary label is used in conjunction with the label used to identify the nucleotide present at a particular variant site. Such secondary labels can be any type of molecule or compound that is detectable (see supra). In other instances, the tag is part of an affinity pair and facilitates separation of the different extension products one from the other, in addition to ftinctioning to separate the extended primer from other extension reaction components as described above. Suitable affinity pairs include those described stiprti in the section on detection methods.

The methods utilizing primers of different size or tagged primers can be used in conjunction with the scheme in which different labels are used for different variant sites. In this way, extension products can be identified and distinguished from one another on the basis of two criteria rather than simply one criterion. For example, in some methods, different nucleotides are attached to different labels. Further, primers include different tags for different variant sites. The different extension products can then be identified and/or separated both according to the different tags and the different labels.

The methods can also be utilized in pooling studies to determine the allele frequency of a variant site in a study population. Typically, in these type of the experiments, the DNA samples from different individuals arc pooled together. Then the method of this invention can be used to analyze the presence of each allele in the mixed templates. By comparing the signal intensities of each allele with a reference set (for example, the hcterozygotes, the homozygotes or a mixture of both at a known ratio), the prevalence of the alleles in the population can be determined. (For a general discussion of pooling studies see, e.g., Breen G. et al., *BioTechniques* 28:464–468 (2000); Risch N. and Teng, J., *Genome Res.* 8:1273–1288 (1998); Shaw, S. H. et al., *Genomer Res.* 8:111–123 (1998); and Scott, D. A. et al., *Am. J. Hum. Genet.* 59:385–391 (1996), each of which is incorporated by reference in its entirety).

VII. Genotyping

A diploid organism contains two copies of each gene. Genotyping of a diploid organism involves the determination of whether the organism contains two copies of the reference allele (a reference-type homozygote), one copy each of the reference and variant allele (i.e., a heterozygote), or contains two copies of the variant allele (i.e., a variant-type homozygote). When conducting a genotyping analysis, the methods of the invention can be utilized to interrogate a single variant site. However, as described above in the section on multiplexing/pooling, the methods can also be used to determine allelic frequency in a group of individuals, as well as the genotype of an individual at many different DNA loci, either on the same gene, different genes or combinations thereof.

Most typically, SNPs consist of two allelic forms, i.e., the variant site includes one of two different nucleotides. The sample can contain nucleic acids representative of the two copies of the target nucleic acid of interest. The analysis is as described supra for biallelic target nucleic acids. In particular, analyses typically are conducted with a mixture of nucleotides that include a labeled extendible nucleotide and a labeled non-extendible nucleotides that are selected to be complementary to the different allelic forms. Formation of a single labeled extended primer indicates that the sample is from a homozygote. The particular labeled nucleotide incorporated signifies whether the sample is from a reference-type or variant-type homozygote. TIhe formation of two labeled extension products indicates that the sample is from a heterozygote.

The methods arc designed to be conducted in a single reaction vessel. Consequently, differentially labeled nucleotides are utilized to distinguish the different allelic forms of the target nucleic acid. For variant sites that have more than two allelic forms, reactions can be conducted as described above for tri-allelic and tetra-allelic nucleic acids.

The ability to use the methods of the invention to make rapid genotyping determinations provides a powerful tool in genetic analysis and ascertaining the susceptibility of an individual to a disease. Individuals that are homozygotes for an allele associated with a particular disease are at higher risk of having the disease than a heterozygote or a homozygote for the other allele. The heterozygote, however, is a carrier of the allele associated with the disease. Such knowledge can be useful in prenatal and other types of medical and genetic counseling, for example.

VIII. Samples

A. Types of Tartget Nucleic Acids

The methods of the present invention can be utilized to determine the identity of a nucleotide at a variety of different types of variant sitcs including, but not limited to, SNPs and mutations such as transitions, transversionis, insertions and deletions. The presence or absence of a target nucleic acid in a sample can be detected generally as the presence or absence of a particular nucleotide at a particular site. Individual nucleotides located at a particular site can also be identified by the methods described herein.

The methods presented are generally applicable to deoxyribonucleic acids, ribonucleic acids, or copolymers thereof. The nucleic acids can be single-stranded or double-stranded. The target nucleic acid can include non-naturally occuiring nucleotide analogs including, for example, deoxyinosine or 7-deaza-2-deoxyguanosine. Such analogs destabilize duplex DNA and allow a primer annealing and extension reaction to occur in double-stranded nucleic acids without completely separating the two strands. In some instances, RNA samples are first reverse transcribed to form cDNA before use.

The target nucleic acid can be only a fraction of a larger nucleic acid or can be present initially as a purified and discrete molecule. Additionally, the target nucleic acid can constitute the entire nucleic acid or can be a fraction of a complex mixture of nucleic acids. The target nucleic acid can be synthesized enzymatically ill vivo, synthesized enzymatically in vitro, or synthesized non-enzymatically.

B. Sources

The target nucleic acid can be from any source. The samples that include the target nucleic acids can be natural or synthetic uslng enzymatic or organic synthesis techniques. Likewise, the sample can be taken from any organism, including but not limited to, plants, microorganisms (e.g., bacteria, fungi and viruses), vertebrates, invertebrates and mammals (e.g., humans, primates, horses, dogs, cows, pigs and sheep).

For assay of genomic DNA, virtually any biological sample (other than pure red blood cells) is suitable. Samples can be obtained from the tissues or fluids of an organism or organisms; samples can also be obtained from cell cultures, tissue homogenates or synthesized as described above. For example, samples can be obtained from whole blood, serum, semen, saliva, tears, urine, fecal material, sweat, buccal, skin, spinal fluid and hair. Samples can also be derived from iil iitiro cell cultures, includinu the growth medium, recombinant cells and cell components. For assay of cDNA or mRNA reverse transcribed to fonn cDNA, the tissue sample is obtained from an organ in which the target nucleic acid is expressed. For example, if the target nucleic acid is a cytochrome P450, the liver is a suitable source. Samples for use in prenatal testing can be obtained from amniotic fluid.

The target nucleic acid(s) can also be obtained from non-living sources suspected of containing matter from living organisms. For example, in the instance of samples obtained for forensic analysis, the target nucleic acids can be obtained from samples of clothing, furniture, weapons and other items found at a crime scene.

C. Sample Preparation

In some instances, the samples contain such a low level of target nucleic acids that it is useful to conduct a pre-amplification reaction to increase the concentration of the target nucleic acids. If samples are to be amplified, amplification is typically conducted using the polymerase chain reaction (PCR) according to known procedures. See generally, *PCR Technology: Principles and Applications for DNA Amplification* (H. A. Erlich, Ed.) Freeman Press, N.Y., N.Y. (1992); *PCR Protocols: A Guide to Methods and Applications* (Innis, et al., Eds.) Academic Press, San Diego, Calif. (1990); Mattila et al., *Nucleic Acids Res.* 19: 4967 (1991 ); Eckert et al., *PCR Metliotis aoudl Applications* 1: 17 (1991); PCR (McPherson et al. Ed.), IRL Press, Oxford; and U.S. Pat. Nos. 4,683,202 and 4,683,195, each of these being incorporated by reference in its entirety. Other suitable amplification methods include the ligase chain reaction (LCR) (see, e.g., Wu and Wallace, *Genomics* 4:560 (1989) and Landegren et al., *Science* 241:1077 (1988); transcription amplification (see, e.g., Kwoh et al., *Proc. Natl. Acad. Sci. USA* 86:1173 (1989)); self-sustained sequence replication (see, e.g., Guatelli et al., *Proc. Natl. Acad. Sci. USA*, 87:1874 (1990)); and nucleic acid based sequence amplification (NABSA) (see, e.g., Sooklnanan, R. and Malek, L., *Bio Technoloqy* 13: 563–65 (1995)), each of which are incorporated by reference in their entirety.

Further guidance regarding nucleic sample preparation is described in Sambrook, et al., *Molecular Cloning: A Laboratory Manual*, $2^{nd}$ Ed., Cold Spring Harbor Laboratory Press, (1989), which is incorporated herein by reference in its entirety.

IX. Kits

Kits for conducting the sequence and genotyping determinations described herein are also provided by the invention. Typically, the kits include one or more primers that specifically hybridize to a segment of a target nucleic acid of interest. Once hybridized to the target nucleic acid, the 3'-end of the primer is adjacent the variant site of the target nucleic acid. Often the primers are designed for use in analyzing one or more SNPs, particularly those correlated with a disease (see supra). The number of primers included in the kit can vary. Generally, the kits include at least 2, 3, 4 or 5 primers. Other kits can include more primers, such as at least 10, 15, 20 or 25 primers. In certain kits, the primers also bear a label or attachment moiety to facilitate the detection/separation process.

The kits also typically include labeled extendible nucleotides and labeled non-extendible nucleotides. Optionally, the nucleotides can be combined to form a mixture. The nucleotides included are typically complementary to the nucleotides that potentially occupy the variant site of interest. The labeled nucleotidcs can bear any of the type of labels described above. Generally, the label is a fluorophore, such as FAM, ROX, TAMRA, R110, R6G, Joe, HEX, TET, Alexa, Cy3 or Cy5.

The kits can include various other components for conducting template-dependent extension reactions including, for example, a polymer-ase and buffers. Kaits can also include the necessary clectrophoretic components to size separate the extension products formed during an analysis. Such components include gel polymers (e.g., agarose), polymerizing agents and buffers. Typically, the kits also include containers for housing the various components and instructions for using the kit components to conduct an analysis.

X. Utility

The methods, compositions and kits of the invention are generally useful for determining the identity of a nucleotide at a variant site. These methods, however, find use in a variety of more specific applications. One use is the identification and detection of point mutations (e.g., somatic point mutations), specifically those mutations correlated with diseases. For example, the methods described herein are useful for identifying whether a nucleic acid from a particular subject includes a wild-type allele or a mutant allele at a particular SNP site. Furthermore, the methods can be utilized to establish the genotype of the individual being tested (i.e., distinguish whether the individual is a reference-type homozygote, a heterozygote or a variant-type homozygote).

The genotyping utility of the present methods makes them useful within the context of medical diagnosis and prognosis. Since many SNPs are associated with various diseases, clinicians can utilize the results of the genotype study to assess the presence of disease, whether an individual is a carrier of disease, the likelihood that an individual will get a particular disease and the likely efficacy of various treatment alternatives.

The methods also have a variety of non-medical uses. Such utilities include detecting pathogenic microorganisms, paternity testing and forensic analysis. The methods can also be used to identify SNPs in non-humans, including, for example, other animals, plants, bacteria and viruses.

These various uses are described more fully below.

A. Correlation Studies

Use of the methods of the present invention to acquire diagnostic information involves obtaining a sample from a number of different individuals known to have a common disease and conducting screening tests to deternine whether they consistently share a common genotype at one or more SNP sites. The results of such screening can be used to establish correlations between certain genotypes and certain diseases.

In a related fashion, the methods of the invention can be used to develop correlations between certain genotypes and patient prognosis. For example, the genotype of a population of individuals suffering from a common disease can be detenlined at one or more SNP sites. The health history of the individuals can be monitored with time to establish correlations between certain genotypes and disease outcomes.

The methods of the invention can also be used to formulate optimal treatment protocols for a particular disease. For example, the ability of an individual to metabolize certain drugs may be associated with a particular genotype(s). The methods described herein can be used to place individuals into groups that share a common phenotype and genotype. The group can then be subdivided into various groups that each receives different forms of treatment. By monitoring the health status of the different treatment groups over time, the most effective treatment program for a particular genotype can be established.

B. Use of Current Methods as Screening and Therapeutic Tool

In instances in which a correlation between a particular genotype and disease state or drug response have already been established, the methods of the invention can be utilized as a diagnostic tool, a prognostic tool and as a means for optimizing treatment.

For patients having symptoms of a disease, the methods of the present invention can be used to determine if the patient has a genotype known to be associated with a disease that commonly causes the symptoms the patient exhibits. For example, if the genotyping methods of the invention show that the individual has a genotype associated with a particular disease and further that the genotype is associated with poor recovery (e.g., a variant-type homozygote), the physician can counsel the patient regarding the likely effectiveness of aggressive treatment options and the option of simply foregoing such treatments, especially if the disease is quite advanced. On the other hand, if the genotype is associated with good recovery, the physician can describe a range of treatment options varying from simply monitoring the disease to see if the condition worsens or more aggressive measures to ensure that the disease is attacked before it gets worse.

The methods of the present invention are also valuable for assessing the actual risk of an individual known to be susceptible to acquiring a disease (e.g., an individual coming from a family that has a history of suffering from a disease). By determining whether the individual is a homozygote for the SNP associated with the disease or a heterozygote, a physician can more accurately assess and counsel the patient regarding the likelihood that the patient will begin suffering from disease, factors involved in triggering the disease and the pros and cons regarding different treatment alternatives.

Similarly, certain methods of the invention can also be used to identify individuals at risk for disease, even though they have no symptoms of disease or no known susceptibilities to disease. An individual in this category would generally have no disease symptoms and have no family history of disease. In such cases, the methods of the present invention can be utilized as a useful preventive screening tool. Using the methods of the present invention, a number of selected SNP sites known to be associated with certain diseases can be interrogated to identify the genotype of the individual at those sites. If a particular genotype were identified that was known to be associated with a particular disease, then a physician could advise the individual regarding the likelihood that the disease would manifest itself and the range of treatment options available.

In yet another application, the present invention can be useful in fomulating optimal treatment for a patient. For example, an individual's response to a drug may be predicted based on his or her genotype. The information enables a physician to prescribe the most effective medication with minimal side effects.

C. Examples of Diseases that can be Monitored

A large number of diseases have been shown to be correlated with particular allelic forms of SNPs. A large number of such SNPs are listed in WO 93/02216 and by Cooper et al. (*Hum. Genet*. 85:55–74 (1990)), both of which are incorporated herein by reference in their entirety. Specific examples of diseases associated with SNPs include: sickle cell anemia and β-thalassemias (mutation in β-globin gene; Antonarakis, *New Eng. J. Med.*, 320:153–163 (1989)), cystic fibrosis (mutation in cystic fibrosis transmembrane receptor (CFTR); see Kerem, et al., *Science* 245:1073–1080 (1989)), hyperlipoproteinemia (mutation in apolipoprotein E gene; see Mahley, *Sciecce* 240:622–630 (1988)), a wide variety of autoimmune diseases (mutations in human major histocompatibility complex; see Thomson, *Ann. Rev. Genet.*, 22:31–50 (1988); Morel et al., *Proc. Natl. Acacd. Sci. USA*, 85:8111–8115 (1988); and Scharf, et al., *Proc. Natl Acad. Sci. USA*, 85:3504–3508 (1988)) and the formation of oncogenes (mutations to the human ras-gene family; see, e.g., Bos et al., *Nature*, 315:726–730 (1985); Fair et al., *Proc. Nail. Acad. Sci. USA*, 85:1629–1633 (1988); and Neri, et al., *Proc. Natl. Acad. Sci. USA*, 85:9268–9272 (1988)). Other genes containing SNPs associated with disease include genes encoding for angiotensinogen, angiotensin converting enzyme, cholesterol ester transfer protein, dopamine receptors, serotonin receptors, and HIV reverse transcriptase (RT).

D. Other Uses

The methods described herein can also be used to identify point mutations in pathogens that could potentially result in altered pathogcnicity or resistance to certain therapeutics. The methods can also be used to identify cells and strains having a desired genetic constitution for use in various biotechnology applications, The methods described herein can also detect the presence of somatic mutations that can result in various diseases, including cancer for example.

With klnowledge gained from the genotyping methods described herein clinicians can conduct prenatal testing uising cells obtained from a fetus to check for a variety of inheritable diseases, such as those diseases associated with the SNPs listed above. The methods can also be used to identify carriers of mutant alleles. Such information can be of use by a couple prior to conception as they evaluate the risks of having a child with certain birth defects or inheritable diseases.

Methods of the invention can also be utilized in various identification applications, such as in the field of forensic medicine or paternal testing. In the case of forensic analysis, polymorphisms in specific genes can be determined in, for example, blood or semen obtained from a crime scene to indicate whether a particular suspect was involved in the crime. In like manner, polymorphism analysis may be utilized in disputes to aid in determining whether a particular individual is the parent of a certain child.

In another application, certain methods of the invention are used in blood typing or tissue classification. Tissue classifications, for example, can be deteniined by identifying polymorphisms specific for a particular individual.

The following examples are provided to illustrate certain aspects of the invention, and should not be construed in any way to limit the scope of the invention.

EXAMPLE 1

Genotyping of the CYP4.2D6. G4268C SNP

1. Materials and Methods

A. Amplification of Target Nucleic Acid

Amplimers were generated through the PCR (Polymerase-Chain-Reaction) process using the HotStart Taq system from Qiagen. The PCR primer binding sites for the SNP analyzed, CYP4.2D6.G4268C, are shown in FIG. 5 in bold type. This particular SNP is a G/C polymorphic site and is indicated by the letter S. Amplifications were conducted according to the manufacturer's recommendations. Primers were obtained from Operon Technologies, Inc. or synthesized using an ABI3948 Nucleic Acid Synthesis & Purification System. Typically, 40 cycles of PCR were performed to give a yield of 5–20 ng/µl DNA.

Excess dNTPs and primers were removed from the PCR products by the addition of exonuclease I and shrimp alkaline phosphatase (USB) at 1 unit/10 µl. After proper mixing, the tubes were incubated at 37°C. for 1 hour followed by 15 minutes at 80 C. At this stage, a small fraction of each sample was analyzed by agarose gel electrophoresis to determine the quality and quantity of the PCR products.

B. Primer Extension

For primer extension, approximately 10 ng of each PCR amplimer was used in a 5-µl reaction containing the following: 1x buffer for Taq FS as recommended by Perkin Elmer, 0.2 µM extension primer, 0.25 unit Taq FS (Perkin Elmer), and dye-labeled dideoxynucleotide triphosphates (NEN Life Science Products, Inc.) at the concentrations indicated in the figure legends. Extension was performed for 30 cycles in a GeneAmp PCR System 9700 (Perkin Elmer). The primer binding site for the SNP studied is underlined in FIG. 5.

C. Analysis of Extension Products

After desalting via ethanol precipitation, the samples were analyzed on a sequencing gel using the ABI 377 Sequencer. Results were plotted as fluorescence intensity versus time. The results shown (see FIGS. 6A and 6B) have been corrected for spectrum overlaps of the two dyes used.

II. Genotyping Results

A set of genotyping experiments were conducted with 7 individuals at the CYP4.2D6.G4268C SNP (Sachise et al., Am. J. Hum. Genet. 6:284–295 (1997), which is incorporated by reference in its entirety). The sequence surrouLnding;, this SNP is shown in FIG. 5. This experiment investigated the ability to utilize mixtules of labeled and unlabelled foims of a deoxynucleotide in combination with a didcoxynucleotide.

A. Combination of Dideoxynucleotides

Figure 6A:
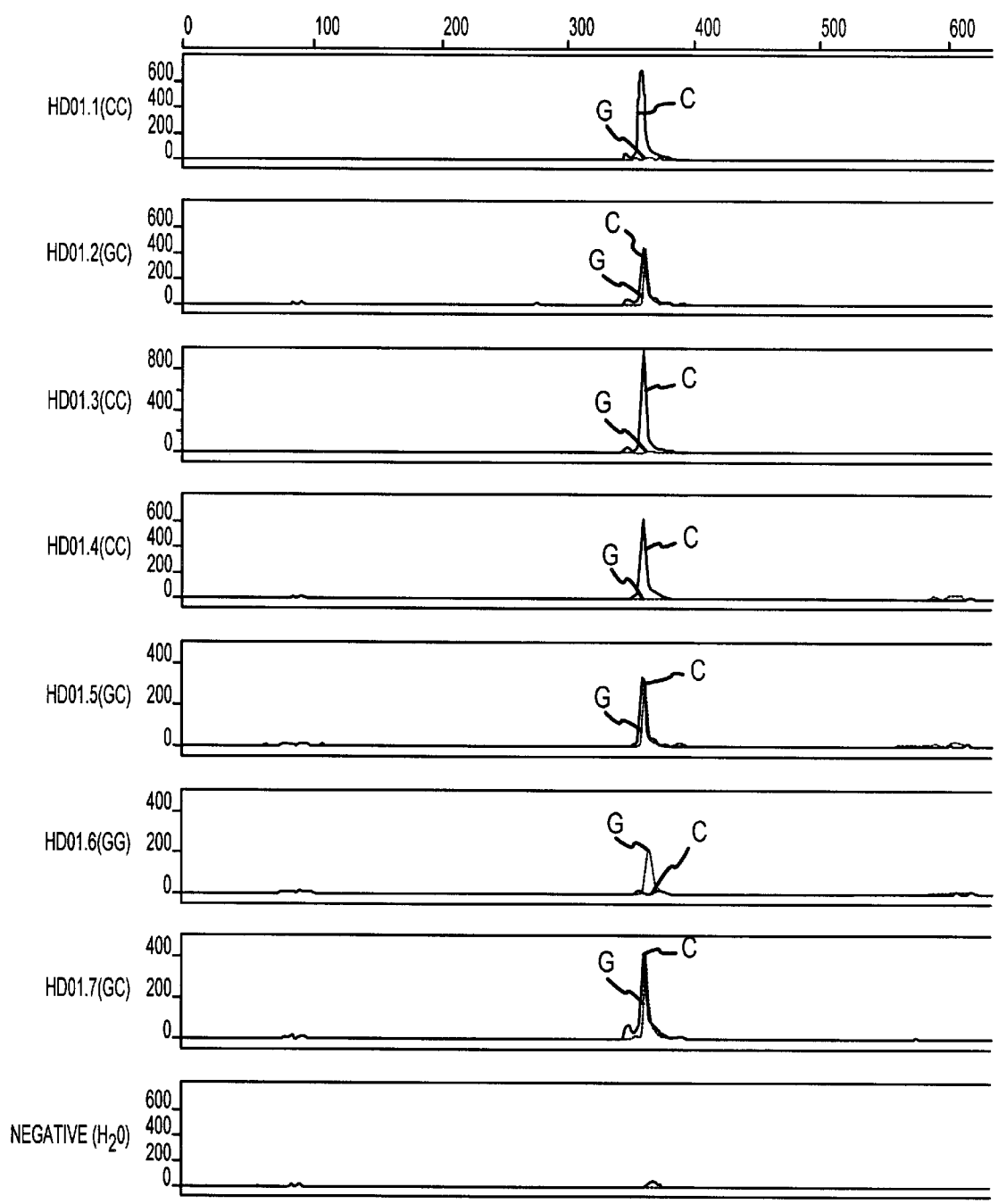
FIG. 6A presents electropherograms as plots of fluorescence intensity versus time for genotyping experiments conducted with 7 different individuals at the CYP4.2D6.G4268C SNP site. This set of experiments was conducted in the presence of only non-extendible nucleotides, specifically a mixture of ddCTP and ddGTP (a 10 nM R110-ddCTP/90 nM ddCTP mixture and a 30 nM TAMRA-ddGTP/70 nM ddGTP mixture). Signals from extension products incorporating R110 label and corresponding to the C allele are represented by the traces labeled with a C. Extension products labeled with TAMRA and corresponding to the G allele are represented by traces labeled G. The genotypes, as indicated in parentheses, were also confirmed by sequencing the amplimers directly.

One experiment was conducted using two dideoxynucleotides, specifically 10 nM R110-ddCTP/90 nM ddCTP and a mixture of 30 nM TAMRA-ddGTP/ 70 nM ddGTP. FIG. 6A presents the clectropherog,rams obtained for the different individuals. Signals from extension products incorporating R110 label and corresponding to the C allele are represented by the traces labeled with a C. Extension products labeled with TAMRA and corresponding to the G allele are represented by traces labeled G. The geniotypes, as indicated in parentheses, were also confirmed by sequencing the amplimers directly.

B. Combination of Dideoxynucleotide and Deoxyiucileotide

Figure 6B:
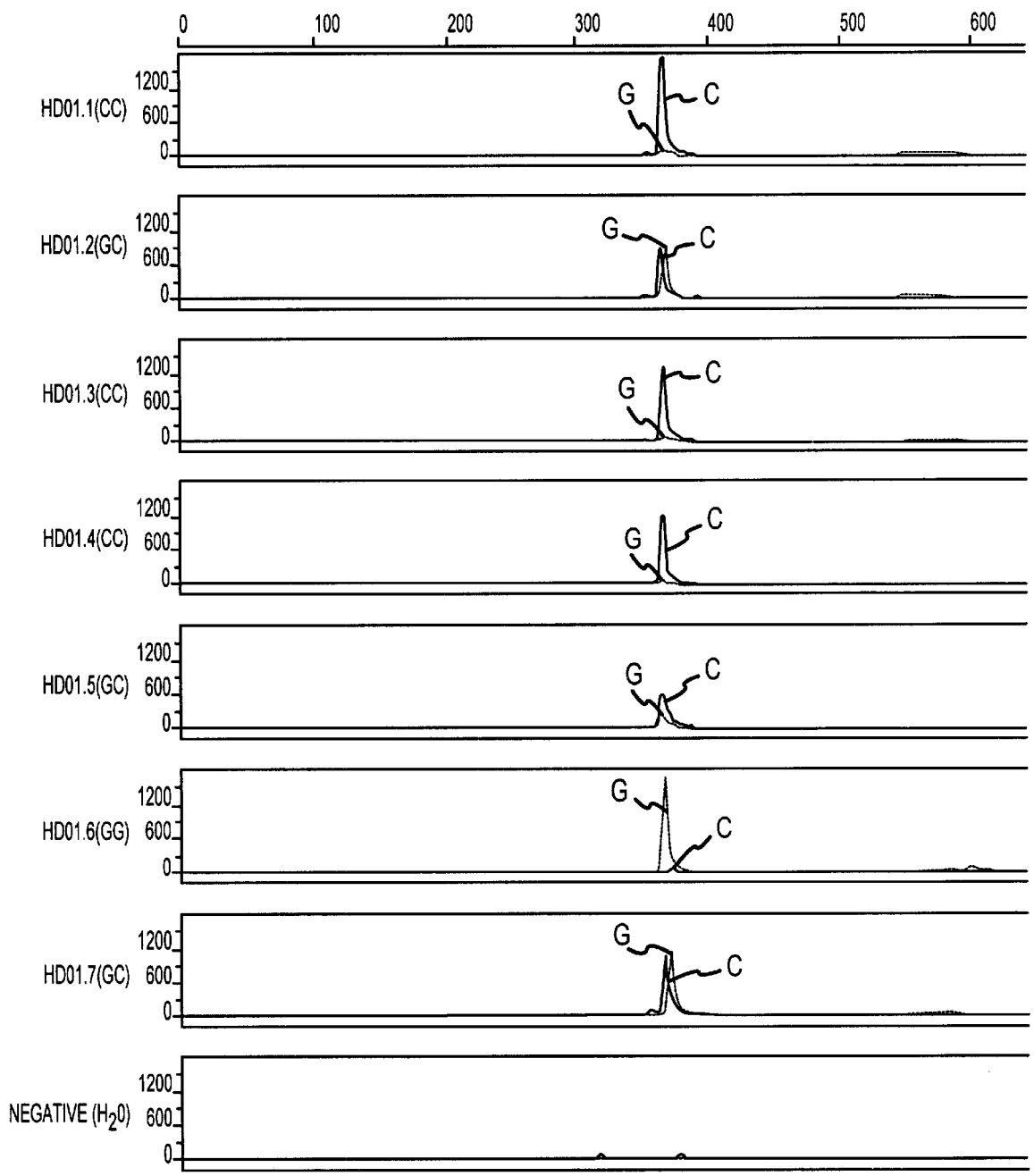
FIG. 6B depicts electropherograms as plots of fluorescence intensity versus time for genotyping experiments conducted with samples from the same 7 individuals described in FIG. 6B at the CYP4.2D6.G4268C SNP site. This experiment, however, was conducted with a mixture of labeled extendible and non-extendible nucleotides. More specifically, experiments were conducted with a 10 nM R110-dCTP/90 nM dCTP mixture and a 30 nM TAMRA-ddGTP/70 nM ddGTP mixture. Extension products incorporating R 110 and generated from the C allele are represented by traces labeled C. Extension products labeled with TAMRA and generated from the G allele are represented by traces labeled G. The correct genotypes are as indicated in parentheses.

Another experiment was conducted using a mixture of a dideoxynucleotide and a deoxynucleotide. Experiments were conducted with a mixture of 10 nM R110-dCTP/90 nM dCTP and a mixture of 30 nM TAMRA-ddGTP/70 nM ddGTP. FIG. 6B depicts the electropherograms obtained for each of the 7 individuals tested. Extension products incorporating R110 and generated from the C allele are represented by traces labeled C. Extension products labeled with TAMRA and generated from the G allele are represented by traces labeled G. The correct genotypes arc as indicated in parentheses. A comparison of FIGS. 6A and 6B demonstrates that a deoxynucleotide can also be used in the primer extension reaction to obtain the correct genotypes.

It is understood that the examples and embodiments described herein are for illustrative purposes only and that various modifications or changes in light thereol will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

What is claimed is:

1. A method of analyzing a variant site of a target nucleic acid, comprising (a) conducting a template-dependent extension reaction comprising extending a primer in the presence of the target nucleic acid and a mixture of nucleotides comprising at least one labeled extendible nucleotide and at least one labeled non-extendible nucleotide, each labeled extendible nucleotide and labeled non-extendible nucleotide being complementary to a different allelic form of the target nucleic acid and optionally differentially labeled, wherein the primer hybridizes to a segment of the target nucleic acid such that the 3'-end of the primer hybridizes adjacent the variant site of the target nucleic acid, whereby if the labeled extendible nuclcotide is complementary to the nucleotide occupying the variant site, the primer is extended by incorporation of the labeled extendible nucleotide, and can be extended further if one or more nucleotides downstream of the variant site are complementary to one of the nucleotides in the mixture, and if the labeled non-extendible nucleotide is complementary to the nucleotide occupying the variant site, the primer is extended by incorporation of the labeled non-extendible nucleotide; and (b) detecting incorporation of labeled nucleotide into the extended primer, the identity of the labeled nucleotide incorporated into the primer indicating the identity of the nucleotide at the variant site, wherein the identity of the incorporated nucleotide is determined from the label borne by the incorporated nucleotide and/or the size of the extended primer.

2. The method of claim 1, wherein the at least one labeled extendible nucleotide is a labeled deoxynucleotide selected from the group consisting of dATP, dTTP, dGTP and dCTP.

3. The method of claim 1, wherein the at least one labeled non-extendible nucleotide is a labeled dideoxynucleotide.

4. The method of claim 1, wherein the at least one labeled extendible nuceleotide is a labeled deoxynucleotide selected from the group consisting of dATP, dTTP, dGTP and dCTP and the at least one labeled non-extendible nucleotide is a labeled dideoxynucleotide.

5. The method of claim 4, wherein the labeled nucleotides are differentially labeled.

6. The method of claim 5, wherein the variant site is a bi-allelic site and the mixture contains a single labeled deoxynucleotide and a single labeled non-extendible nucleotide.

7. The method of claim 5, wherein the variant site is a tri-allelic site and the mixture contains a single labeled deoxynucleotide and two labeled non-extenidible nucleotides.

8. The method of claim 5, wherein the variant site is a tri-allelic site and the mixture contains two labeled deoxynucleotides and a single labeled non-extendible nucleotide.

9. The method of claim 5, wherein the variant site is a tetra-allelic site and the mixture contains a single labeled deoxynuclCotidc and three labeled non-extendible nucleotides.

10. The method of claim 5, wherein the variant site is a tetra-allelic site and the mixture contains two labeled deoxynucleotides and two labeled non-extendible nucleotides.

11. The method of claim 5, wherein the variant site is a tetra-allelic site and the mixture contains three labeled deoxynucleotides and one labeled non-extendible nucleotide.

12. The method of claim 1, wherein the 3'-end of the primer hybridizes immediately adjacent the variant site.

13. The method of claim 1, wherein the primer extension reaction is conducted under themocycling conditions.

14. The method of claim 1, wherein the label borne by the labeled nucleotides is selected from the group consisting of a fluorophore, a chromophore, a chemiluminescent agent, a radioisotope, an enzyme substrate, an electron dense reagent, a magnetic particle, an electrochemically active moiety and a mass label.

15. The method of claim 14, wherein the label borne by the labeled nucleotides is a fluorescent dye.

16. Thie method according to claim 15, wherein the fluorescent dye is selected from the group consisting of FAM, ROX, TAMRA, R110, R6G, Joe, HEX, TET, Alexa, Cy3 and Cy5.

17. The method of claim 1, wherein extended primer is separated from the labeled nucleotides prior to detecting incorporation of labeled nucleotide into the primer.

18. The method of claim 17, wherein separation is achieved by a size-based separation technique.

19. The method of claim 18, wherein the sized-based separation technique is gel electrophoresis or high performance liquid chromatography.

20. The method of claim 17, wherein extended primer is denatured from the target nucleic acid prior to separating extended primer from the labeled nucleotides.

21. The method of claim 17, wherein the primer bears an attachment moiety that is a first member of a binding pair and separation comprises contacting the primer with a support attached to a second member of the binding pair, whereby the primer becomes immobilized to the support via interaction between the first and second binding pair members.

22. The method of claim 1, wherein the primer bears a primer label different from the labels borne by the labeled nucleotides such that the extended primer bears the primer label and label from the incorporated labeled nucleotide.

23. The method of claim 22, wherein the primer label and the label from the incorporated nucleotide comprise a donor fluorophore and an acceptor fluorophore and detecting comprises detecting a change in fluorescence in the donor and/or acceptor.

24. The method of claim 15, wherein the detection of incorporation is performed by fluorescence polarization.

25. The method of claim 5, wherein (a) multiple copies of the primer are provided and the target nucleic acid is a first and/or second target nucleic acid contained in a sample from a diploid subject, the first and/or second target nucleic acid differing at the site of variation, whereby if the first target nucleic acid is present, at least one copy of the primer is extended by incorporation of the labeled deoxynucleotide and if the second target nucleic acid is present, at least one copy of the primer is extended by incorporation of the labeled non-extendible nucleotide; and (b) detecting comprises detecting incorporation of labeled deoxynucleotide and/or labeled non-extenidiblc nticleotide into the primer copies, incorporation of only labeled deoxynuclCotide or labeled non-extendible nucleotide indicating that the subject is a homozygote, whereas incorporation of labeled deoxynucleotide and labeled non-extenidible nucleotide indicate that the subject is a heterozygote.

26. The method of claim 25, wherein the labeled deoxynucleotide and labeled non-extendible nucleotide bear different fluorescent labels that emit at different wavelengths, and detection comprises detection of fluorescence, detection of fluorescence at a single wavelength indicating that the subject is a homozygote and detection of fluorescence at two wavelengths indicating that the subject is a heterozygote.

27. The method of claim 25, wherein:

(a) one or more nuclCotidcs immediately downstream of the variant site of the target nucleic acids are the same as a nuLcleotidc potentially at the variant site and the labeled deoxynucleotidc is selected to be complementary to the one or more downstream nucleotides, whereby if the labeled deoxynucleotidc is complementary to the nucleotide at the variant site of either the first or second target nucleic acid, then the primer is further extended to include additional labeled deoxynuLcleotide such that the first and second target nucleic acid gencerate different sized extension products; and (b) detecting comprises detecting the presence or absence of different sized extension products.

28. A method for analyzing variant sites in one or more target nucleic acids, comprising:

(a) conducting a plurality of template-dependent extension reactions in the presence of a plurality of different primers, wherein different primers hybridize adjacent to different variant sites of the one or more target nucleic acids and are differentially labeled, each extension reaction comprising
  (i) contacting a sample containing the target nucleic acid(s) with one of the different labeled primers, wherein the 3'-end of the primer hybridizes adjacent to but not including the variant site of one of the target nucleic acids, and
  (ii) exposing the primer to a mixture of nucleotides comprising at least one labeled extendible nuclcotidc and at least one labeled non-extendible nucleotide under conditions whereby
    if the labeled extendible nucleotide is complementary to the nucleotide occupying the variant site, the primer is extended by incorporation of labeled extendible nucleotide, and can be extended further if one or more nucleotides downstream of the variant site are complementary to one of the nucleotides in the mixture, and
    if the labeled non-extendible nucleotide is complementary to the nucleotide occupying the variant site, the primer is extended by incorporation of labeled non-extendible nucleotide,
    whereby the extension reactions generate a plurality of different extension products, extension products generated from different variant sites being distinguishable on the basis of the different labels borne by the extended primers; and
(b) detecting the incorporation of labeled nucleotides into the extension products as an indication of the nucleotides occupying the site of variation in the target nucleic acids, wherein the identity of the incorporated nucleotide is determined from the label borne by the incorporated nucleotide and/or the size of the extended primer.

29. The method of claim 28, wherein the different variant sites are different variant sites on the same target nucleic acid or different sites on different target nucleic acids and the extension reactions are conducted in a single reaction vessel.

30. The method of claim 28, wherein the label borne by the labeled nucleotides and the label borne by labeled primers are selected from the group consisting of a fluorophore, a chromophore, a chemiluminescenit agent, a radioisotope, an enzyme substrate, an electron dense reagent, a magnetic particle, an electrochemically active moiety and a mass label.

31. The method of claim 28, wherein different primers bear different mass labels and detecting comprises separating different extension products according to size.

32. The method of claim 28, wherein
(a) the different labels borne by the different primers are different fluorophores and the labeled nucleotides bear different fluorophores, such that the fluorophores borne by an extension product form a donor and acceptor pair; and
(b) detecting comprises detecting a change in an emission from the donor and/or acceptor for the different donor and acceptor pairs.

33. The method of claim 28, wherein detection is performed by fluorescence polarization.

34. A kit for analyzing a variant site in a target nucleic acid, comprising:

(a) at least one labeled extendible nucleotide and at least one labeled non-extendible nucleotide, the nucleotides complementary to different allelic forms of the target nucleic acid; and
(b) at least one primer, each primer hybridizing to a segment of the target nucleic acid such that the 3' end of the primer is adjacent the variant site of the target nucleic acid.

35. The kit of claim 34, further comprising a polymerase.

36. The kit of claim 34, wherein the label borne by the labeled nucleotides is a fluorophore.

37. The kit of claim 36, wherein the fluorophore is selected from the group consisting of FAM, ROX, TAMRA, R110, R6G, Joe, HEX, TIETI, Alexa, Cy3 and Cy5.

38. The kit of claim 34, wherein the primer bears a primer label.

39. The kit of claim 38, wherein the primer label is a fluorophore, the fluorophore borne by the nucleotides and the fluorophore borne by the primer comprising donor and acceptor pairs.

40. The kit of claim 34, wherein the primer is at least five primers, each primer hybridizing adjacent a different variant site in the target nucleic acid.

41. The kit of claim 40, wherein each variant site is a site correlated with a disease.

42. The method of claim 1, wherein detection of incorporated labeled nucleotide is performed without separating labeled nucleotides from extended primer.

43. A method of analyzing a variant site of a target nucleic acid, comprising:
(a) conducting a template-dependent extension reaction comprising extending a primer in the presence of the target nucleic acid and a mixture of nucleotides comprising at least one labeled extendible nucleotide and at least one labeled non-extendible nucleotide, each labeled extendible nucleotide and labeled non-extendible nucleotide being complementary to a different allelic form of the target nucleic acid and differentially labeled, and wherein the primer hybridizes to a segment of the target nucleic acid such that the 3'-end of the primer hybridizes adjacent the variant site of the target nucleic acid, whereby
  if the labeled extendible nucleotide is complementary to the nucleotide occupying the variant site, the primer is extended by incorporation of the labeled extendible nucleotide, and
  if the labeled non-extendible nucleotide is complementary to the nucleotide occupying the variant site, the primer is extended by incorporation of the labeled non-extendible nucleotide; and
(b) detecting incorporation of labeled nucleotide into the extended primer, the identity of the labeled nucleotide incorporated into the primer indicating the identity of the nucleotide at the variant site, wherein the identity of the incorporated nucleotide is determined from the label borne by the incorporated nucleotide.

44. The method of claim 43, wherein the at least one labeled non-extendible nucleotide is a labeled dideoxynucleotide.

45. The method of claim 43, wherein the label borne by the labeled nucleotides is selected from the group consisting of a fluorophore, a chromophore, a chemiluminescent agent, a radioisotope, an enzyme substrate, an electron dense reagent, a magnetic particle, an electrochemically active moiety and a mass label.

* * * * *

UNITED STATES PATENT AND TRADEMARK OFFICE
CERTIFICATE OF CORRECTION

PATENT NO. : 6,355,433 B1  Page 1 of 5
DATED : March 12, 2002
INVENTOR(S) : Hua Xu and Alexander N. Glazer It is certified that error appears in the above-identified patent and that said Letters Patent is hereby corrected as shown below:

<u>Title page,</u>
*Assistant Examiner,* please add: -- *Attorney, Agent, or Firm* - Townsend and Townsend and Crew LLP --.

<u>Column 1,</u>
Line 47, the "oligonucleotidc" should read -- oligonucleotide --.
Line 48, the "EP-32931 1" should read -- EP-329311 --.
Line 55, the "U .E. M," should read -- U.E.M., --.

<u>Column 3,</u>
Line 63, the "analyzing, target" should read -- analyzing target --.
Line 64, the "foiis" should read -- forms --.

<u>Column 4,</u>
Line 63, the "Such" should read -- such --.
Line 63, the "polymcrase" should read -- polymerase --.

<u>Column 5,</u>
Line 14, the "priner" should read -- primer --.
Line 28, the "ntucleic" should read -- nucleic --.
Line 29, the "Kanchisa" should read -- Kanehisa --.
Line 29, the "*Acicls*" should read -- *Acids* --.
Line 35, the "nuicleic" should read -- nucleic --.
Line 40, the "Strinnent" should read -- Stringent --.
Line 43, the "higoler" should read -- higher --.
Line 63, the "nueleotide" should read -- nucleotide --.

<u>Column 6,</u>
Line 41, the "dideoxynuclcotides" should read -- dideoxynucleotides --.

<u>Column 8,</u>
Line 22, the "cxtendible" should read -- extendible --.

<u>Column 10,</u>
Line 8, the "whiclh" should read -- which --.
Line 45, the "complementaiy" should read -- complementary --.

<u>Column 11,</u>
Line 66, the "nuclcotide" should read -- nucleotide --.

UNITED STATES PATENT AND TRADEMARK OFFICE
CERTIFICATE OF CORRECTION

PATENT NO. : 6,355,433 B1
DATED : March 12, 2002
INVENTOR(S) : Hua Xu and Alexander N. Glazer It is certified that error appears in the above-identified patent and that said Letters Patent is hereby corrected as shown below:

Column 12,
Line 1, the "nuclcotides" should read -- nucleotides --.
Line 7, the "fonn" should read -- form --.
Line 17, the "unrcacted" should read -- unreacted --.
Line 49, the "arc" should read -- are --.
Line 50, the "polynucleotidc" should read -- polynucleotide --.
Line 55, the "of-the" should read -- of the --.
Line 57, the "fomi" should read -- form --.

Column 13,
Line 40, the "hoomogenous" should read -- homogenous --.

Column 14,
Line 65, the "dimethylaminollaphthyl" should read -- dimethylaminonaphthyl --.

Column 15,
Line 1, the "pheniyl" should read -- phenyl --.
Line 1, the "isocyanatocoumarini" should read -- isocyanatocoumarin --.
Line 5, the "carbocvanine" should read -- carbocyanine --.
Line 7, the "tetranmethyl" should read -- tetramethyl --.
Line 8, the "carboxyrhodaminc" should read -- carboxyrhodamine --.
Line 10, the "carboxyrhodaninie" should read -- carboxyrhodamine --.
Line 15, the "Amershamii Phaniacia" should read -- Amersham Pharmacia --.
Line 16, the "Eutgene" should read -- Eugene --.
Line 22, the "Del(ker" should read -- Dekker --.
Line 25, the "*Organiic*" should read -- *Organic* --.
Line 54, the "fonnation" should read -- formation --.

Column 16,
Line 12, the "tenninates" should read -- terminates --.
Line 17, the "tenninates" should read -- terminates --.
Line 24, the "nuclcotide" should read -- nucleotide --.
Line 24, the "utilizing, the" should read -- utilizing the --.
Line 35, the "non-extendiblc" should read -- non-extendible --.
Line 37, the "(dW4TP)" should read -- ($dW^4TP$) --.
Line 51, the "nulceotides" should read -- nucleotides --.
Line 58, the "arc" should read -- are --.

UNITED STATES PATENT AND TRADEMARK OFFICE
CERTIFICATE OF CORRECTION

PATENT NO.   : 6,355,433 B1
DATED        : March 12, 2002
INVENTOR(S)  : Hua Xu and Alexander N. Glazer It is certified that error appears in the above-identified patent and that said Letters Patent is hereby corrected as shown below:

Column 17,
Line 3, the "nuclcotidc" should read -- nucleotide --.
Line 30, the "and,or" should read -- and/or --.
Line 64, the "ftinctioning" should read -- functioning --.
Line 67, the "stiprti" should read -- supra --.

Column 18,
Line 15, the "arc" should read -- are --.
Line 19, the "hcterozygotes" should read -- heterozygotes --.
Line 50, the "nucleotides" should read -- nucleotide --.
Line 55, the "Tlhe" should read -- The --.
Line 58, the "arc" should read -- are --.

Column 19,
Line 8, the "Tartget" should read -- Target --.
Line 11, the "sitcs" should read -- sites --.
Line 12, the "transversionis" should read -- transversions --.
Line 21, the "occuiring" should read -- occurring --.
Line 33, the "ill" should read -- in --.
Line 38, the "usling" should read -- using --.
Line 52, the "iil iitiro" should read -- in vitro --.
Line 52, the "includinu" should read -- including --.
Line 54, the "fonn" should read -- form --.

Column 20,
Line 10, the "*Metliotis aoudl*" should read -- *Methods and* --.
Line 21, the "Sooklnanan" should read -- Sooknanan --.
Line 22, the *"Technoloqy" should* read -- *Technology* --.
Line 55, the "polymer-ase" should read -- polymerase --.
Line 55, the "Kaits" should read -- Kits --.
Line 56, the "clectrophoretic" should read -- electrophoretic --.

Column 21,
Line 37, the "detenlined" should read -- determined --.

UNITED STATES PATENT AND TRADEMARK OFFICE
CERTIFICATE OF CORRECTION

PATENT NO. : 6,355,433 B1
DATED : March 12, 2002
INVENTOR(S) : Hua Xu and Alexander N. Glazer It is certified that error appears in the above-identified patent and that said Letters Patent is hereby corrected as shown below:

Column 22,
Line 36, the "fomulating" should read -- formulating --.
Line 53, the "*Sciecce*" should read -- *Science* --.
Line 56, the "*Acacd.*" should read -- *Acad.* --.
Line 57, the "*Natl* "should read -- *Natl.* --.
Line 60, the "Fair" should read -- Farr --.
Line 61, the "*Nail.*" should read -- *Natl.* --.

Column 23,
Line 4, the "pathogcnicity" should read -- pathogenicity --.
Line 10, the "klnowledge" should read -- knowledge --.
Line 11, the "herein" should read -- herein, --.
Line 12, the "uising" should read -- using --.
Line 29, the "deteniined" should read -- determined --, Column 24,
Line 9, the "Sachise" should read -- Sachse --.
Line 12, the "surrouLnding;," should read -- surrounding --.
Line 13, the "mixtules" should read -- mixtures --.
Line 15, the "didcoxynucleotide" should read -- dideoxynucleotide --.
Line 19, the "clectropherog,rams" should read -- electropherograms --.
Line 24, the "geniotypes" should read -- genotypes --.
Lines 27-28, the "Deoxyiucileotide" should read -- Deoxynucleotide --.
Line 38, the "arc" should read -- are --.
Line 44, the "thereol" should read -- thereof --.

Column 25,
Line 4, the "pathogcnicity" should read -- pathogenicity --.
Line 24, the "nuceleotide" should read -- nucleotide --.
Line 35, the "non-extenidible" should read -- non-extendible --.
Line 42, the "deoxynuclCotidc" should read -- deoxynucleotide --.
Line 53, the "themocycling" should read -- thermocycling --.
Line 61, the "Thie" should read -- The --.

UNITED STATES PATENT AND TRADEMARK OFFICE
CERTIFICATE OF CORRECTION

PATENT NO. : 6,355,433 B1
DATED : March 12, 2002
INVENTOR(S) : Hua Xu and Alexander N. Glazer It is certified that error appears in the above-identified patent and that said Letters Patent is hereby corrected as shown below:

Column 26,
Lines 38-39, the "non-extenidiblc nticleotide" should read -- non-extendible nucleotide --.
Line 40, the "deoxynuclCotide" should read -- deoxynucleotide --.
Line 43, the "non-extenidible" should read -- non-extendible --.
Line 53, the "nuclCotidcs" should read -- nucleotides --.
Line 55, the "nuLcleotidc" should read -- nucleotide --.
Line 56, the "deoxynucleotidc" should read -- deoxynucleotide --.
Line 58, the "deoxynucleotidc" should read -- deoxynucleotide --.
Lines 61-62, the "deoxynuLcleotide" should read -- deoxynucleotide --.
Line 63, the "gencerate" should read -- generate --.

Column 27,
Line 13, the "nuclcotidc" should read -- nucleotide --.

Column 28,
Line 13, the "TIETI" should read -- TET --.

Signed and Sealed this

First Day of October, 2002

Attest:

JAMES E. ROGAN
Attesting Officer    Director of the United States Patent and Trademark Office